US008993842B2

(12) United States Patent
Dupree et al.

(10) Patent No.: US 8,993,842 B2
(45) Date of Patent: Mar. 31, 2015

(54) MODIFIED XYLAN PRODUCTION

(75) Inventors: Paul Dupree, Cambridge (GB); Godfrey Preston Miles, Cambridge (GB)

(73) Assignee: Cambridge Enterprise Limited (GB)

( * ) Notice: Subject to any disclaimer, the term of this patent is extended or adjusted under 35 U.S.C. 154(b) by 101 days.

(21) Appl. No.: 12/679,309

(22) PCT Filed: Sep. 17, 2008

(86) PCT No.: PCT/GB2008/050830
§ 371 (c)(1),
(2), (4) Date: Mar. 20, 2010

(87) PCT Pub. No.: WO2009/037502
PCT Pub. Date: Mar. 26, 2009

(65) Prior Publication Data
US 2011/0185449 A1 Jul. 28, 2011

(30) Foreign Application Priority Data
Sep. 21, 2007 (GB) .................................. 0718377.5

(51) Int. Cl.
*C12N 15/82* (2006.01)
*C12N 15/63* (2006.01)
*C12N 15/09* (2006.01)
*A01H 5/00* (2006.01)
*C12N 9/10* (2006.01)
*C13K 13/00* (2006.01)
*C07K 14/415* (2006.01)

(52) U.S. Cl.
CPC .......... *C12N 15/8246* (2013.01); *C12N 9/1051* (2013.01); *C13K 13/002* (2013.01); *C07K 14/415* (2013.01); *C12N 15/8245* (2013.01); *A23V 2002/00* (2013.01)
USPC ........... 800/284; 800/285; 800/286; 800/295; 435/320.1; 435/468; 536/23.1; 536/23.6

(58) Field of Classification Search
None
See application file for complete search history.

(56) References Cited

U.S. PATENT DOCUMENTS 5,922,579 A * 7/1999 Fagerstrom et al. ............ 435/99

FOREIGN PATENT DOCUMENTS

| WO | WO98/55596 | 12/1998 |
| WO | WO03/014365 | 2/2003 |

OTHER PUBLICATIONS

Brown et al 2005 The Plant Cell 17:2281-2295, provided by Applicant.*
Pena et al., "*Arabidopsis* irregular xylem8 and irregular xylem9: Implications for the Complexity of Glucuronoxylan Biosynthesis", XP-002509991, The Plant Cell, vol. 19, pp. 549-563, Feb. 2007.
Zhou et al., "Molecular Characterization of PoGT8D and PoGT43B, Two Secondary Wall-Associated Glycosyltransferases in Poplar", Plant Cell Pysiol, pp. 689-699, 2007.
Persson et al., "The *Arabidopsis* irregular xylem8 Mutant Is Deficient in Glucuronoxylan and Homogalacturonan, Which Are Essential for Secondary Cell Wall Integrity", The Plant Cell, vol. 19, pp. 237-255, Jan. 2007.
Brown et al., "Identification of Novel Genes in *Arabidopsis* Involved in Secondary Cell Wall Formation Using Expression Profiling and Reverse Genetics", XP-002509992, The Plant Cell, vol. 17, pp. 2281-2295, Aug. 2005.
Aspeborg et al., "Carbohydrate-Active Enzymes Involved in the Secondary Cell Wall Biogenesis in Hybrid Aspen", XP-002496123, Plant Physiology, vol. 137, pp. 983-997, Mar. 2005.
GB Search Report for Application No. GB0718377.5 dated Jan. 22, 2008.
PCT International Search Report and Written Opinion for International Application No. PCT/GB2008/050830 dated Jan. 27, 2009.

* cited by examiner

*Primary Examiner* — Brent T Page
(74) *Attorney, Agent, or Firm* — Tumey L.L.P.

(57) ABSTRACT

Methods and means for producing xylan structures in plants having a non-native saccharide moiety substitution side chain component, plants and plant cells comprising modified xylan structures, methods of identifying mutant plants comprising xylan structures in plants having a non-native saccharide moiety substitution pattern side chain component, uses thereof, and isolated xylan structures and uses thereof.

22 Claims, 7 Drawing Sheets

MODIFIED XYLAN PRODUCTION

FIELD OF INVENTION

Figure 1:
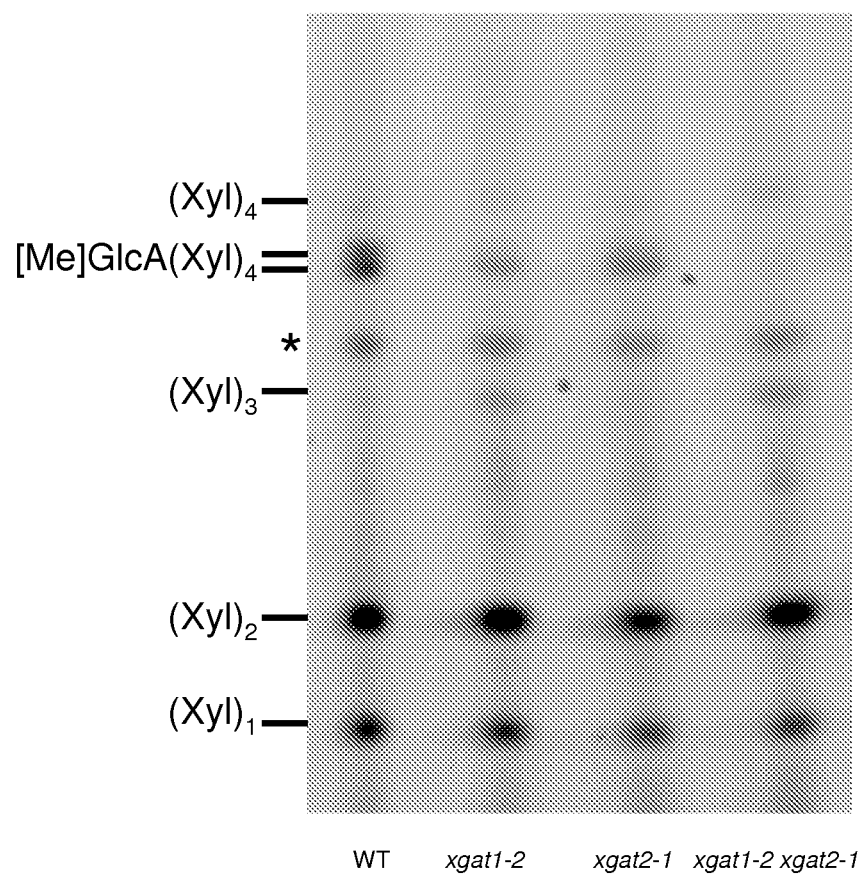

The present invention relates to methods for screening for altered xylan saccharide side chain substitution components and altered xylan saccharide side chain substitution enzymic activity and/or patterning in plant cell material, transformed plant cell material and methods for producing modified xylans in plant cell material.

In particular, the invention relates to methods for screening for modified xylan saccharide side chain substitution activity in plants, transformed plant cell material comprising xylan molecules having altered 4-O-methyl glucuronic acid and/or glucuronic acid side chain content wherein the activity of xylan glucuronyl transferase (XGAT) enzymes is altered, methods for producing modified xylans comprised in plant cell material, the genetic material required therefor, such as DNA and RNA, vectors, host cells, methods of introduction of genetic material into plant cells, and uses thereof.

BACKGROUND OF INVENTION

For the purposes of the present invention "glucuronic acid" and "4-O-methyl glucuronic acid" are referred to hereinbelow by the terms "GlcA" and "MeGlcA", respectively. The term "[Me]GlcA" is used as a collective noun herein to denote both GlcA and MeGlcA.

Native xylan is a hemicellulose that is often cross-linked to lignin via [Me]GlcA side chains (e.g. Balakshin et al. 2007, Holzforschung, 61, 1-7). Native xylan is also tightly associated with cellulose microfibrils. Native xylan is of value in certain industries but its extraction is complicated by a range of covalent and non-covalent chemical linkages to other components of the cell wall, such as linkages to [Me]GlcA. Typically, enzymatic and chemical means are used inter alia, to disrupt the side chain linkages, enabling the extraction of xylan. Extraction processes are generally costly and give rise to side products that are undesirable.

Enzymatic methods are also used to depolymerise the cellulose and hemicelluloses into soluble hexose and pentose sugars. Depolymerisation (also referred to in the art as "saccharification") of xylan requires a multiplicity of enzymes to break the backbone and side chain linkages. Some of the products of enzymatic treatments are not able to be used by many organisms used in fermentation or in bio-processing to produce liquid transport fuels such as ethanol or butanol.

Extracted native xylan is used inter alia in paper production and modified xylan-containing plant material has potential for use in, inter alia, the production of sugars and indirectly, in the production of liquid transport fuels such as ethanol via fermentation of the sugars. Cellulose fibrils, used inter alia in paper and other materials, are damaged by the processes of extraction of xylan and other hemicellulose from the fibrils.

The prior art appears to be silent about the precise role that xylan saccharide side chain modifying enzymes, such as XGAT enzymes, play in secondary cell wall structure, and their function does not appear to have been accurately elucidated.

Brown D. M. et al The Plant Cell, Vol. 17, 2281-2295, August 2005 describes a study relating to mutant *Arabidopsis thaliana* plants comprising insertions into a so-called glycosyl transferase 8-like gene, identified as At3g18660, which allegedly resulted in a plant that had a weak stem, a feature known to be a characteristic of known secondary cell wall mutants. However, the elucidation of the function of At3g18660 and the role it plays in secondary cell wall synthesis does not appear to be described by Brown D. M. et al. Indeed, At3g18860 is not described as a xylan glucuronyl transferase and no putative industrial use for At3g18660 is contemplated.

Pena M. J. et al The Plant Cell, Vol. 19:549-563, February 2007 describe studies on mutant plants of *Arabidopsis thaliana* in which the presence of "wood-associated GTs", such as IRX8 are present. The study is confined to looking at IRX8 and IRX9 genes and their effect on glucuronoxylan chemistry and structure. *Arabidopsis thaliana* genes At4g33330 and At3g18660 are mentioned as homologs (sic) of "wood associated GTs" but that appears to be all that Pena M. J. et al supra say about them.

Zhong R. et al The Plant Cell Vol. 17, 3390-3408, December 2005 describe studies on inter alia mutant plants of *Arabidopsis thaliana* Fragile Fiber8 which is thought by the authors to encode a glucuronyl transferase that is involved in secondary wall synthesis. Zhong R et al report that the GlcA component of xylan is missing. It is not reported that the level of overall [Me]GlcA substitution is unchanged. The data presented by Zhong R et al indicates that they were unable to distinguish if the level of overall [Me]GlcA substitution had changed. In wild type plants, the xylose in the xylan is about 7% substituted with MeGlcA and 3% with GlcA; 10% overall. Thus, the overall proportion of xylose substitution is no different to wild type plants. The overall substitution pattern is unlike the new xylan structures created using the XGATs of the invention in which the absolute substitution level of [Me]GlcA on the xylans created using At4g33330 and/or At3g18660 can be varied depending on the level of expression or the level of gene silencing that may be generated.

SUMMARY OF INVENTION

Plants that are produced by methods of the invention have xylans comprising a novel [Me]GlcA composition, that is to say the sum of the MeGlcA and GlcA is different to that of wild type plants or mutant plants described in the prior art.

Furthermore, plants comprising modified xylans of the invention may be more amenable to end uses such as paper pulp production; animal feeds for herbivorous animals, such as domesticated animals; improved dietary fibre component of food for human consumption; use as biomass for liquid fuel production; and in the extraction of plant products of interest, such as sugars that may be readily converted to fermentable sugars, since the extraction of plant products may be simpler than that of extraction processes used on conventional plants. These and other advantages of plants of the invention comprising modified xylans will become apparent from the following description and examples.

According to the present invention there is provided a transformed plant cell comprising a xylan structure having a non-native saccharide moiety substitution pattern side chain component, such as a [Me]GlcA side chain component.

Also encompassed within the ambit of the invention are transformed plants, transformed plant parts, or transformed plant cells that may be derived from a transformed plant tissue of the invention, such as transformed callus, transformed somatic embryo, transformed pre-embryogenic masses, transformed root tip cultures and the like.

"Non-native" in the context of the present invention means that the xylan structure has a modified saccharide moiety substitution side chain component, such as a [Me]GlcA side chain component that does not or is not known to occur in a native plant of the same species as that of the transformed plant cell or transformed plant. "Non-native" as applied to mutant plants known in the art, that is to say a mutant plant of the same species that has not been transformed using classical DNA or RNA insertion or deletion techniques common to molecular biology, and especially plant molecular biology, has a similar meaning to that described for a transformed plant (see above). Thus, a mutant plant known in the art refers to naturally-occurring mutants and also to mutants that have been created using techniques, such as chemical mutagenesis, e.g using ethylmethanesulphonate (EMS), or physical procedures e.g. γ-ray irradiation, which typically do not employ classical DNA or RNA insertion or deletion techniques known in the art. Mutant plants may be identified, for example, by employing targeting induced local lesions in genome ("TILLING") procedures as described by Colbert et al Plant Physiol, June 2001, Vol 126, pp. 480-484. In TILLING procedures DNA is collected from populations of plants which possess random point mutations which may be as a result of natural variation or via artificial induction by man. By selectively pooling the DNA samples and amplifying them with labelled primers, mismatched heteroduplexes form between the wild type DNA strands and the mutant DNA strands. The mismatched heteroduplexes may then be incubated with an endonuclease that is able to cleave the heteroduplex at mismatched sites and the resultant products are identified, for example on a sequencing gel. By analysing the data, plants can be identified which harbour mutations in genes that are known to be involved in saccharide substitution patterning on xylans or are suspected of being involved in such activity. Such plants may then be investigated for their saccharide substitution patterning on xylans using techniques described herein.

Preferably, transformed plant cells of the invention are provided wherein the non-native saccharide moiety substitution side chain component pattern is located on up to 50% of the backbone xylose residues of the xylan structure. Such saccharide side chain components, for example the xylan GlcA and MeGlcA side chains of plants of the invention may be found substituting the backbone xylose residues at a proportion that is different from that which may be found in a corresponding plant of the same species of the prior art. Suitable substitution proportions for saccharide moiety substitution patterning (for example [Me]GlcA), that are achievable by the present invention include up to 50%, up to 30%, up to 20%, such as from 0.001% up to 1%, 2%, 3%, 4%, 5%, 6%, 7%, 8%, 9%, 10%, 11%, 12%, 13%, 14%, or 15% and so on, provided that the actual novel saccharide moiety substitution patterning component (for example the patterning for the [Me]GlcA component) is not known in the relevant plant species of the prior art.

In a further aspect of the invention, there is provided a nucleotide sequence encoding an antisense RNA molecule complementary to a sense mRNA molecule encoding for a protein having an enzymic activity in xylan side chain substitution, which nucleotide sequence is under transcriptional control of a promoter and a terminator, both promoter and terminator being capable of functioning in plant cells.

The nucleotide sequence encoding the antisense RNA molecule can be of any length provided that the antisense RNA molecule transcribable therefrom is sufficiently long so as to be able to form a complex with a sense mRNA molecule encoding for a protein having an enzymic activity in xylan side chain substitution. Suitable proteins having enzymic activity in xylan side chain substitution reactions include xylan glucuronyl transferases (XGATs), such as the *Arabidopsis thaliana* sequences, At4g33330 and At3g18660, At1g77130, At1g08990, At1g54940 (from *Arabidopsis thaliana*), PttGT8A, PttGT8B and PttGT8C (from poplar), CAK29728 (partial sequence from *Pica abies*, conifer), and other XGAT homologues or orthologues thereof from other species, such as Os03g0184300, Os01g0880200, Os05g0426400, OsI_010047, AAK92624 (from Rice) AK250038 (from Barley), AY110752, (from Maize), and ABE88903 (From *Medicago truncatula*). Thus, it is thought that the antisense RNA molecule or short sequences derived from it in planta, in vivo, or in vitro, such as short interfering RNA (siRNA), form complexes that are capable of interfering with the mRNA of the protein. Thus, the synthesis of functional protein(s), such as XGAT proteins, having enzymic activity in xylan side chain substitution is prevented or substantially inhibited. As a consequence of the interference of the antisense RNA, enzyme activity of XGAT protein(s) involved in xylan side chain substitution is decreased.

For the purposes of the present description "nucleotide sequence" will be referred to as DNA unless there is different indication. The DNA encoding the antisense RNA can be from about 20 nucleotides in length up to the length of the relevant mRNA produced by the cell. The length of the DNA encoding the antisense RNA will preferably be from 20 to 1500, more preferably from 20 to 1000 nucleotides in length. When the interfering antisense RNA is interfering siRNA, the length of the siRNA strand is from 20 to 30 nucleotides in length and may be 20, 21, 22, 23, 24, 25, 26, 27, 28, 29 or 30 bases in length. The preferred source of antisense RNA for DNA constructs of the present invention is DNA showing substantial identity or similarity to the genes or fragments thereof of proteins having XGAT enzymic activity. Thus the encoding DNA of constructs of the present invention may be selected from nucleic acid molecules encoding XGATS, such as proteins selected from the group from the group At4g33330, At3g18660, At1g77130, At1g08990, At1g54940 (from *Arabidopsis thaliana*), PttGT8A, PttGT8B and PttGT8C (from poplar), CAK29728 (partial sequence from *Pica abies*, conifer), and other XGAT homologues or orthologues thereof from other species, such as Os03g0184300, Os01g0880200, Os05g 0426400, OsI_010047, AAK92624 (from Rice) AK250038 (from Barley), AY110752, (from Maize), ABE88903 (from *Medicago truncatula*) and fragments thereof such as enzymically active fragments thereof, or orthologues thereof from other plant species or fragments thereof such as enzymically active fragments thereof.

In a further aspect of the invention there is provided a nucleotide sequence (nucleotide sequence according to the invention) comprising a transcriptional regulatory sequence, a sequence under the transcriptional control thereof which encodes an RNA which consists of a plurality of subsequences, characterized in that the RNA subsequences are antisense RNAs to mRNAs of proteins having an enzymic activity in xylan side chain substitution in plant cells.

The nucleotide sequence may encode in antisense orientation an RNA having any number of subsequences which may comprise more than one siRNA sequence; may comprise at least one siRNA sequence and at least one longer RNA sequence; may comprise at least one longer RNA sequence. Preferably, the number of subsequences is up to 6, and more preferably from 1 to 3.

The nucleotide sequence of the invention also includes complementary sense polynucleotide sequences of the antisense sequences of the invention, that when transcribed in plant material, leads to an increase in xylan side chain substitution and hence a disproportionately high overall level of xylan side chain substitution relative to the level found in native plants of the same species or of a corresponding species. The skilled addressee will also appreciate that the overexpression of such sense sequences for XGAT proteins may also elicit siRNA mediated XGAT gene silencing, giving rise to xylan side chain substitution patterns wherein the overall level of xylan side chain substitution is lower than that of native plants of the same species.

Preferably, the RNA encoded by the contiguous sequence comprises a cleavage site, such as a ribozyme or restriction enzyme site such as XbaI, SalI, KpnI or the like, between two of the subsequences so that the RNA can be cleaved into regions comprising said subsequences, or even into the subsequences per se. Naturally, the skilled addressee will appreciate that the subsequences contained within the RNA encoded by the contiguous sequence resulting from such cleavage will not contain a 5' cap or a ribozome binding site and will thus not be translated when present in a eukaryotic cell, such as a plant cell.

The invention still further provides a nucleotide sequence which is similar to the above disclosed antisense RNA sequences. By "similar" is meant a test sequence which is capable of hybridising to a sequence which is complementary to the inventive nucleotide sequence. When the test and inventive sequences are double stranded the nucleic acid constituting the test sequence preferably has a Tm within 20° C. of that of the inventive sequence. In the case wherein the test and inventive sequences are mixed together and denatured simultaneously, the Tm values of the sequences are preferably within 10° C. of each other. More preferably the hybridization is performed under stringent conditions, with either the test or inventive DNA preferably being supported. Thus either a denatured test or inventive sequence is preferably first bound to a support and hybridization is effected for a specified period of time at a temperature of between 50° and 70° C. in double strength SSC (2×NaCl 17.5 g/l and sodium citrate (SC) at 8.8 g/l) buffered saline containing 0.1% sodium dodecyl sulphate (SDS) followed by rinsing of the support at the same temperature but with a buffer having a reduced SSC concentration. Depending upon the degree of stringency required, and thus the degree of similarity of the sequences, such reduced concentration buffers are typically single strength SSC containing 0.1% SDS, half strength SSC containing 0.1% SDS and one tenth strength SSC containing 0.1% SDS. Sequences having the greatest degree of similarity are those the hybridization of which is least affected by washing in buffers of reduced concentration. It is most preferred that the test and inventive sequences are so similar that the hybridization between them is substantially unaffected by washing or incubation in one tenth strength sodium citrate buffer containing 0.1% SDS.

The invention still further provides a nucleotide sequence which is complementary to one which hybridizes under stringent conditions with the above disclosed nucleotide sequences.

The invention still further provides the use of the sequence according to the invention, whether "naked" or present in a DNA construct or biological vector in the production of eukaryotic cells, particularly plant cells having a modified xylan content as described herein.

The invention still further provides a method of inducing an under expression of an enzymic protein of xylan side chain substitution in plant cells comprising introducing into such cells a nucleotide sequence according to the invention, or a construct or vector containing it.

The invention still further provides a method of inhibiting the production of at least one XGAT enzyme in a eukaryotic cell comprising introducing into the said cell a nucleotide sequence comprising a transcriptional regulatory sequence and a sequence contiguous therewith and under the transcriptional control thereof, which contiguous sequence encodes an RNA which consists of a single subsequence or a plurality of subsequences, characterized in that the subsequence or subsequences have the sequences of antisense RNA's to mRNA's of proteins having an enzymic activity in xylan side chain substitution in a plant.

Examples of the nucleotide sequences of the invention are provided below. These examples relate to the production of plants, such as *Arabidopsis thaliana* plants having an altered xylan component of the invention.

1. The nucleotide sequence of the invention may encode an mRNA which consists—in the 5' to 3' direction—of (i) a promoter, (ii) at least one cDNA in reverse orientation i.e. 3' to 5' orientation, (III) a terminator, (iv) optionally a further promoter, (v) the coding region of a marker gene, such as GFP and (vi) optionally a further stop codon. When such a sequence is introduced into the cells of plants, the sequence encoding the mRNA is transcribed. The region of the thus transcribed mRNA which encodes the marker gene is translated, whilst the region of the mRNA which encodes the cDNA is not.

2. The nucleotide sequence of the invention may encode an mRNA which consists—in the 5' to 3' direction—of (i) a promoter, (ii) the coding region of a marker gene, such as GFP, (iii) a translation stop codon, (iv) optionally a further start codon, (v) a region encoding at least one cDNA in reverse orientation i.e. 3' to 5' orientation and (vi) optionally a further stop codon. When such a sequence is introduced into the cells of plants, the sequence encoding the mRNA is transcribed. The region of the thus transcribed mRNA which encodes the marker gene is translated, whilst the region of the mRNA which encodes the cDNA in reverse orientation i.e. 3' to 5' orientation is not translated.

3. The nucleotide sequence of the invention may encode an mRNA which comprises in the 5' to 3' direction (i) a promoter, (ii) a cDNA in reverse orientation i.e. 3' to 5' orientation, (iii) a terminator, (iv) a promoter, (v) the coding region of a marker gene, such as GFP, (vi) a terminator, (vii) a promoter, (viii) a second cDNA in reverse orientation i.e. 3' to 5' orientation, (ix) a terminator. When such a sequence is introduced into the cells of plants, the sequences encoding (ii) and (viii) are transcribed. The region of the thus transcribed mRNA which encodes the marker gene, such as GFP is translated, whilst the regions of the mRNA encoding the cDNA is not.

Suitable cDNAs that may be used in plants and constructs of the invention include XGAT cDNAs, that encode proteins selected from the group At4g33330 and At3g18660 or At1g77130, At1g08990, At1g54940 (from *Arabidopsis thaliana*), PttGT8A, PttGT8B and PttGT8C (from poplar), CAK29728 (partial sequence from *Pica abies*, conifer), and other XGAT homologues or orthologues thereof from other species, such as Os03g0184300, Os01g0880200, Os05g 0426400, OsI_010047, AAK92624 (from Rice) AK250038 (from Barley), AY110752, (from Maize), and ABE88903 (From *Medic ago truncatula*) that are capable of altering saccharide side chain substitution on xylan when introduced into a plant cell comprised in a plant. The anti-sense sequences of At4g33330 and/or At3g18660 may be placed in other plant species such as members of the Brassicaceae, for example, curly kale, cabbages, cauliflowers, broccolis and the like.

The cDNA's encoding a protein of use in the invention, such as, At4g33330 and/or At3g18660, in a vector containing at least one type of promoter that is operable in a plant cell, for example, an inducible or a constitutive promoter operatively linked to a first and/or second nucleic acid sequence or nucleic acid sequence component as herein defined and as provided by the present invention. As discussed, this enables control of expression of the polynucleotide of the invention.

The invention also provides plants transformed with polynucleotide sequences or constructs and methods including introduction of such polynucleotide nucleic acid sequences or constructs into a plant cell and/or induction of expression of said first or second nucleic acid sequence or construct within a plant cell, e.g. by application of a suitable stimulus, such as an effective exogenous inducer.

The term "inducible" as applied to a promoter is well understood by those skilled in the art. In essence, expression under the control of an inducible promoter is "switched on" or increased in response to an applied stimulus (which may be generated within a cell or provided exogenously). The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus. The preferable situation is where the level of expression increases upon application of the relevant stimulus by an amount effective to alter a phenotypic characteristic. Thus an inducible (or "switchable") promoter may be used which causes a basic level of expression in the absence of the stimulus which level is too low to bring about a desired phenotype (and may in fact be zero). Upon application of the stimulus, expression is increased (or switched on) to a level, which brings about the desired phenotype. One example of an inducible promoter is the ethanol inducible gene switch disclosed in Caddick et al (1998) Nature Biotechnology 16: 177-180. A number of inducible promoters are known in the art.

Chemically regulated promoters can be used to modulate the expression of a gene or a polynucleotide sequence of the invention in a plant through the application of an exogenous chemical regulator. Depending upon the objective, the promoter may be a chemically inducible promoter, where application of the chemical induces gene expression, or a chemical-repressible promoter, where application of the chemical represses gene expression. Chemically inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemically regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2): 247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789, 156), herein incorporated by reference.

Where enhanced expression of XGAT sequences of the invention (either in antisense orientation or in sense orientation) in particular tissues is desired, tissue-specific promoters can be utilized. Tissue-specific promoters include those described by Yamamoto et al. (1997) *Plant J.* 12(2)255-265; Kawamata et al. (1997) *Plant Cell Physiol.* 38(7):792-803; Hansen et al. (1997) *Mol. Gen. Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol. Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505.

So-called constitutive promoters may also be used in the methods of the present invention. Constitutive promoters include, for example, CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. application Ser. No. 08/409,297), and the like. Other constitutive promoters include those in U.S. Pat. Nos. 5,608,149; 5,608, 144; 5,604,121; 5,569,597; 5,466,785; 5,399,680; 5,268,463; and 5,608,142.

Naturally, the man skilled in the art will appreciate that terminator DNA sequences will be present in constructs used in the invention. A terminator is contemplated as a DNA sequence at the end of a transcriptional unit which signals termination of transcription. These elements are 3'-non-translated sequences containing polyadenylation signals, which act to cause the addition of polyadenylate sequences to the 3' end of primary transcripts. For expression in plant cells the nopaline synthase transcriptional terminator (A. Depicker et al., 1982, J. of Mol. & Applied Gen. 1:561-573) sequence serves as a transcriptional termination signal.

Those skilled in the art are well able to construct vectors and design protocols for recombinant nucleic acid sequences or gene expression. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology*, Second Edition, Ausubel et al. eds., John Wiley & Sons, 1992. The disclosures of Sambrook et al. and Ausubel et al. are incorporated herein by reference. Specific procedures and vectors previously used with wide success upon plants are described by Bevan (Nucl. Acids Res. 12, 8711-8721 (1984)) and Guerineau and Mullineaux (1993) (Plant transformation and expression vectors. In: Plant Molecular Biology Labfax (Croy R R D ed.) Oxford, BIOS Scientific Publishers, pp 121-148).

Naturally, the skilled addressee will appreciate that each introduced nucleic acid sequence, such as a genomic DNA sequence or a cDNA sequence coding for at least one saccharide moiety side chain component modifying protein, such as an XGAT sense sequence, and designed to over-express XGAT and thereby initiate activation of the siRNA gene silencing mechanisms of a plant cell, that is to say a sequence oriented in the 5' to 3' direction behind its promoter (e.g. sense At4g33330 and/or sense At3g18660), will be under regulatory control of its own exogenous promoter and terminator.

Selectable genetic markers may facilitate the selection of transgenic plants and these may consist of chimaeric genes that confer selectable phenotypes such as resistance to antibiotics such as kanamycin, neomycin, hygromycin, puramycin, phosphinotricin, chlorsulfuron, methotrexate, gentamycin, spectinomycin, imidazolinones and glyphosate or they may consist of other markers, such as proteins capable of fluorescence, such as green fluorescent protein (GFP).

When introducing selected nucleic acid sequences according to the present invention into a cell, certain considerations must be taken into account, well known to those skilled in the art. The nucleic acid to be inserted should be assembled within a construct, which contains effective regulatory elements, which will drive transcription. There must be available a method of transporting the construct into the cell. Once the construct is within the cell membrane, integration into the endogenous chromosomal material either will or will not occur. Finally, as far as plants are concerned the target cell type must be such that cells can be regenerated into whole plants.

Plants transformed with DNA segments containing sequences of interest as provided herein may be produced by standard techniques, which are already known for the genetic manipulation of plants. DNA can be transformed into plant cells using any suitable technology, such as a disarmed Ti-plasmid vector carried by *Agrobacterium* exploiting its natural gene transfer ability (EP-A-270355, EP-A-0116718, NAR 12(22) 8711-87215 1984), particle or micro projectile bombardment (U.S. Pat. No. 5,100,792, EP-A-444882, EP-A-434616) microinjection (WO 92/09696, WO 94/00583, EP 331083, EP 175966, Green et al. (1987) *Plant Tissue and Cell Culture*, Academic Press), electroporation (EP 290395, WO 8706614) other forms of direct DNA uptake (DE 4005152, WO 9012096, U.S. Pat. No. 4,684,611), liposome mediated DNA uptake (e.g. Freeman et al. *Plant Cell Physiol.* 29: 1353 (1984)), or the vortexing method (e.g. Kindle, *PNAS U.S.A.* 87: 1228 (1990d) Physical methods for the transformation of plant cells are reviewed in Oard, 1991, *Biotech. Adv.* 9: 1-11.

Thus once a nucleic acid sequence or gene has been identified, it may be reintroduced into plant cells using techniques well known to those skilled in the art to produce transgenic plants of the appropriate phenotype.

*Agrobacterium* transformation is widely used by those skilled in the art to transform dicotyledonous species.

Production of stable, fertile transgenic plants in almost all economically relevant monocot plants is also now routine: (Toriyama, et al. (1988) *Bio/Technology* 6, 1072-1074; Zhang, et al. (1988) *Plant Cell Rep.* 7, 379-384; Zhang, et al. (1988) *Theor. Appl. Genet.* 76, 835-840; Shimamoto, et al. (1989) *Nature* 338, 274-276; Datta, et al. (1990) *Bio/Technology* 8, 736-740; Christou, et al. (1991) *Bio/Technology* 9, 957-962; Peng, et al. (1991) International Rice Research Institute, Manila, Philippines 563-574; Cao, et al. (1992) *Plant Cell Rep.* 11, 585-591; Li, et al. (1993) *Plant Cell Rep.* 12, 250-255; Rathore, et al. (1993) *Plant Molecular Biology* 21, 871-884; Fromm, et al. (1990) *Bio/Technology* 8, 833-839; Gordon-Kamm, et al. (1990) *Plant Cell* 2, 603-618; D'Halluin, et al. (1992) *Plant Cell* 4, 1495-1505; Walters, et al. (1992) *Plant Molecular Biology* 18, 189-200; Koziel, et al. (1993) *Biotechnology* 11, 194-200; Vasil, I. K. (1994) *Plant Molecular Biology* 25, 925-937; Weeks, et al. (1993) *Plant Physiology* 102, 1077-1084; Somers, et al. (1992) *Bio/Technology* 10, 1589-1594; WO92/14828). In particular, *Agrobacterium* mediated transformation is now a highly efficient alternative transformation method in monocots (Hiei et al. (1994) *The Plant Journal* 6, 271-282).

The generation of fertile transgenic plants has been achieved in the cereals rice, maize, wheat, oat, and barley (reviewed in Shimamoto, K. (1994) *Current Opinion in Biotechnology* 5, 158-162.; Vasil, et al. (1992) *Bio/Technology* 10, 667-674; Vain et al., 1995, *Biotechnology Advances* 13 (4): 653-671; Vasil, 1996, *Nature Biotechnology* 14 page 702). Wan and Lemaux (1994) *Plant Physiol.* 104: 37-48 describe techniques for generation of large numbers of independently transformed fertile barley plants.

The generation of fertile transgenic trees has been achieved in poplar (Halpin, C et al. TREE GENETICS & GENOMES 3 (2): 101-110 APR 2007, Song J Y, PLANT AND CELL PHYSIOLOGY 47 (11): 1582-1589 NOV 2006), loblolly pine (reviewed in Boerjan W CURRENT OPINION IN BIOTECHNOLOGY 16 (2): 159-166 APR 2005), eastern white pine (*Pinus strobus* L.) Tang W PLANT CELL REPORTS 26 (5): 673-682 MAY 2007)

Micro projectile bombardment, electroporation and direct DNA uptake are preferred where *Agrobacterium* is inefficient or ineffective. Alternatively, a combination of different techniques may be employed to enhance the efficiency of the transformation process, e.g. bombardment with *Agrobacterium* coated micro particles (EP-A-486234) or micro projectile bombardment to induce wounding followed by co-cultivation with *Agrobacterium* (EP-A-486233).

Following transformation, a plant may be regenerated, e.g. from single cells, callus tissue or leaf discs, as is standard in the art. Almost any plant can be entirely regenerated from cells, tissues and organs of the plant. Available techniques are reviewed in Vasil et al., *Cell Culture and Somatic Cell Genetics of Plants, Vol. I, II and III, Laboratory Procedures and Their Applications*, Academic Press, 1984, and Weiss Bach and Weiss Bach, *Methods for Plant Molecular Biology*, Academic Press, 1989.

The particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention, nor is the choice of technique for plant regeneration.

The invention further encompasses a host cell transformed with vectors or constructs as set forth above, especially a plant or a microbial cell. Thus, a host cell, such as a plant cell, including nucleotide sequences of the invention as herein indicated is provided. Within the cell, the nucleotide sequence may be incorporated within the chromosome.

Also according to the invention there is provided a plant cell having incorporated into its genome at least a nucleotide sequence, particularly heterologous nucleotide sequences, as provided by the present invention under operative control of regulatory sequences for control of expression as herein described. The coding sequence may be operably linked to one or more regulatory sequences which may be heterologous or foreign to the nucleic acid sequences employed in the invention, such as not naturally associated with the nucleic acid sequence(s) for its (their) expression. The nucleotide sequence according to the invention may be placed under the control of an externally inducible promoter to place expression under the control of the user. A further aspect of the present invention provides a method of making such a plant cell involving introduction of nucleic acid sequence(s) contemplated for use in the invention or a suitable vector including the sequence(s) contemplated for use in the invention into a plant cell and causing or allowing recombination between the vector and the plant cell genome to introduce the said sequences into the genome. The invention extends to plant cells containing a nucleotide sequence according to the invention as a result of introduction of the nucleotide sequence into an ancestor cell.

The term "heterologous" may be used to indicate that the gene/sequence of nucleotides in question have been introduced into said cells of the plant or an ancestor thereof, using genetic engineering, ie by human intervention. A transgenic plant cell, i.e. transgenic for the nucleotide sequence in question, may be provided. The transgene may be on an extra-genomic vector or incorporated, preferably stably, into the genome. A heterologous gene may replace an endogenous equivalent gene, ie one that normally performs the same or a similar function, or the inserted sequence may be additional to the endogenous gene or other sequence. An advantage of introduction of a heterologous gene is the ability to place expression of a sequence under the control of a promoter of choice, in order to be able to influence expression according to preference. Furthermore, mutants, variants and derivatives of the wild-type gene, e.g. with higher or lower activity than wild type, may be used in place of the endogenous gene. Nucleotide sequences heterologous, or exogenous or foreign, to a plant cell may be non-naturally occurring in cells of that type, variety or species. Thus, a nucleotide sequence may include a coding sequence of or be derived from a particular type of plant cell or species or variety of plant, placed within the context of a plant cell of a different type or species or variety of plant. A further possibility is for a nucleotide sequence to be placed within a cell in which it or a homologue is found naturally, but wherein the nucleotide sequence is linked and/or adjacent to nucleic acid which does not occur naturally within the cell, or cells of that type or species or variety of plant, such as operably linked to one or more regulatory sequences, such as a promoter sequence, for control of expression. A sequence within a plant or other host cell may be identifiably heterologous, exogenous or foreign.

Plants which include a plant cell according to the invention are also provided, along with any part or propagule thereof, seed, selfed or hybrid progeny and descendants. Particularly provided are transgenic field crop plants and transgenic tree species, which have been engineered to carry genes identified as stated above. Examples of suitable plants include *Nicotania tabacum* and other *Nicotiana* species, sugar beet, sugar cane, wheat, barley, (corn) maize, rice, Miscanthus, Switch grass (*Panicum virgatum*) sorghum, and cotton. Examples of tree species amenable to transformation according to the teaching of the invention include poplar, loblolly pine, Hybrid Aspen: *Populus tremula×Populus tremuloides*, Hybrid poplar: *P. tremula×P. alba, Eucalyptus* species such as *Eucalyptus globulus* (Southern Blue gum), *Eucalyptus camaldulensis×Eucalyptus globulus, Eucalyptus grandis, Eucalyptus gunnii, pinus* species, silver fir, balsam fir, Japanese fir, Siberian fir, Japanese Cyprus, European larch, Western larch, Siberian larch, European spruce, White spruce, Sitka spruce, Western white pine, European Black pine, Longleaf pine, Ponderosa pine, Radiata pine, Red pine, Pitch pine, Eastern white pine, Scots pine, Matai, Douglas fir, European white birch, paper birch, yellow poplar, white willow, black willow, American elm, and mountain elm. Especially preferred transformed plants and/or transformed plant cells of the invention are selected from poplar, loblolly pine, *pinus* species selected from those listed herein, eucalyptus species selected from *Eucalyptus globulus* (Southern Blue gum), *Eucalyptus camaldulensis×Eucalyptus globulus, Eucalyptus grandis, Eucalyptus gunnii*, wheat, barley, (corn) maize, rice, Miscanthus, Switch grass (*Panicum virgatum*), sugar cane.

In addition to a plant, the present invention provides any clone of such a plant, seed, selfed or hybrid progeny and descendants, and any part of any of these, such as cuttings, seed. The invention provides any plant propagule, that is, any part which may be used in reproduction or propagation, sexual or asexual, including cuttings, seed and so on. Also encompassed by the invention is a plant which is a sexually or asexually propagated off-spring, clone or descendant of such a plant, or any part or propagule of said plant, off-spring, clone or descendant.

Native, non-transformed plants can also be screened and analysed for naturally occurring mutations in nucleic acid sequences of interest that are employed in saccharide moiety substitution of xylans in native populations of wild type plants. Furthermore, plants in which mutations have been induced, for example via conventional mutagenesis or via TDNA insertion as outlined herein may also be screened for alterations in nucleotide sequences known to be or suspected of being employed in the saccharide moiety substitution of xylans, that is to say, in populations of such conventionally mutagenised plants. Furthermore, the level of saccharide substitution that may be present in such plants comprising mutations in nucleic acid sequences may be screened using procedures similar to those outlined herein and the level of saccharide moiety substitution of xylan can be determined as outlined herein. Initially, plant populations of interest may be screened using appropriate nucleic acid sequences of interest that are known to be employed in saccharide moiety substitution of xylans, such as, nucleic acid sequences encoding XGAT proteins of the group selected from At4g33330, At3g18660, At1g77130, At1g08990, At1g54940 (from *Arabidopsis thaliana*), PttGT8A, PttGT8B and PttGT8C (from poplar), CAK29728 (partial sequence from *Pica abies*, conifer), and other XGAT homologues or orthologues thereof from other species, such as Os03g0184300, Os01g0880200, Os05g 0426400, OsI_010047, AAK92624 (from Rice) AK250038 (from Barley), AY110752, (from Maize), and ABE88903 (From *Medicago truncatula*).

Thus, in a further aspect of the invention there is provided a method for screening plants in a given plant population for mutant alleles involved in the saccharide moiety substitution of xylans that comprises:
  i) obtaining nucleic acid samples from the plants;
  ii) screening the nucleic acid samples with at least one known marker sequence of a nucleic acid sequence that is employed in saccharide substitution of xylan;
  iii) identifying plants that comprise at least one mutant allele relative to the known marker sequence of step ii).

The marker sequence may be selected from nucleic acid sequences that are known to be employed in saccharide substitution of xylans such as XGAT sequences encoding proteins selected from the group At4g33330, At3g18660, At1g77130, At1g08990, At1g54940 (from *Arabidopsis thaliana*), PttGT8A, PttGT8B and PttGT8C (from poplar), CAK29728 (partial sequence from *Pica abies*, conifer), and other XGAT homologues or orthologues thereof from other species, such as Os03g0184300, Os01g0880200, Os05g 0426400, OsI_010047, AAK92624 (from Rice) AK250038 (from Barley), AY110752, (from Maize), ABE88903 (From *Medicago truncatula*), depending on the species of plant under investigation.

Once plants possessing mutant alleles have been identified their xylan content, and in particular, the saccharide substitution pattern of their xylans may be determined, for example, in accordance with methods as outlined herein (Goubet et al; Vicky Wong, PhD thesis, University of Cambridge 2005)

Thus, the present invention further encompasses the isolated, modified xylan product of novel mutagenised plants and/or the isolated, modified xylan product of naturally-occurring mutant plants that may be identified in plant populations as outlined herein.

In addition to the above outlined methods of screening for and/or identifying plants comprising novel saccharide moiety substitution patterns on their xylans that where a TDNA library may be used in the creation of plant lines with a view to obtaining novel saccharide moiety substitution patterns on their xylans, techniques for generating mutant plants comprising T-DNA inserts in nucleic acid sequences or of locating mutant plants comprising T-DNA inserts may be employed. Accordingly, as a further aspect of the invention there is provided a method of identifying mutant plants that comprises i) extracting nucleic acid;
ii) screening the extracted nucleic acid for native DNA and T-DNA inserts using primers;
iii) amplifying the screened nucleic acid of step ii) via PCR; and
iv) comparing the PCR products against a reference standard.

The skilled addressee will appreciate that once a mutant plant has been identified according to this embodiment of the invention, the saccharide moiety substitution pattern on the xylan structure may be investigated and confirmed using methods such as PACE, as outlined herein.

In a further embodiment of the invention there is provided a method of generating a mutant plant comprising a modified saccharide substitution pattern on its xylan structure that comprises:

i) inserting a DNA sequence into a nucleic acid sequence encoding an enzyme that has enzyme activity in saccharide moiety substitution patterning on xylan into a viable plant cell; and
ii) generating a plant from said plant cell.

The inserted DNA sequence may be a T-DNA sequence or a nonsense DNA sequence that either renders the targeted nucleic acid sequence ("gene" sequence) at least partially dysfunctional, or substantially dysfunctional, that is to say, incapable of giving rise to a fully functional enzyme capable of giving rise to a native saccharide substitution pattern on the xylan structure. Such incapacitated nucleic acids may be fully dysfunctional. Preferably, the incapacitated nucleic acids are fully dysfunctional, that is to say, incapable of giving rise to a native saccharide substitution pattern on a xylan structure. Such plants may be generated using standard protocols and procedures as outlined herein and are applicable to the provision of plants comprising anti-sense nucleic acid sequences of interest or sequences that give rise to "co-suppression", such sequences typically being linked to the generation of siRNA species.

The present invention also encompasses the modified xylan product of a transformed plant according to the invention as disclosed herein or obtainable in accordance with the information and suggestions herein. Those skilled in the art are well able to construct vectors and design protocols and systems suitable for the carrying out of the invention.

Use of either of the terms "homology" and "homologous" herein does not imply any necessary evolutionary relationship between compared sequences, in keeping for example with standard use of terms such as "homologous recombination" which merely requires that two nucleotide sequences are sufficiently similar to recombine under the appropriate conditions.

The teaching of all references cited herein is incorporated in its entirety into the present description.

DETAILED DESCRIPTION OF THE INVENTION

There now follow non-limiting examples and figures illustrating the invention.

FIG. 1: PACE gel showing reduction in substitution of xylan in xgat mutants. In xgat1-2 and the double mutant xgat1/xgat2, $(Xyl)_3$ and $(Xyl)_4$ increase as $[Me]GlcA(Xyl)_4$ decreases. Xgat2-1 shows a small reduction in $[Me]GlcA(Xyl)_4$. (*) unspecific band.

Figure 2:
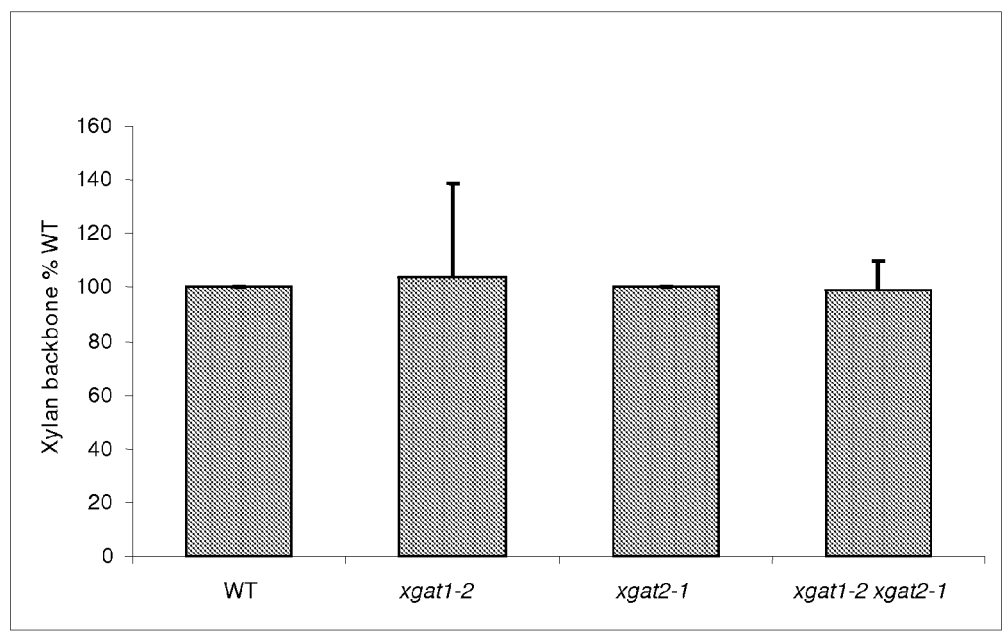

FIG. 2: Quantity of xylan backbone in xgat mutants is unchanged in relation to wild type plants. N=2 to 4 biological replicates.

Figure 3:
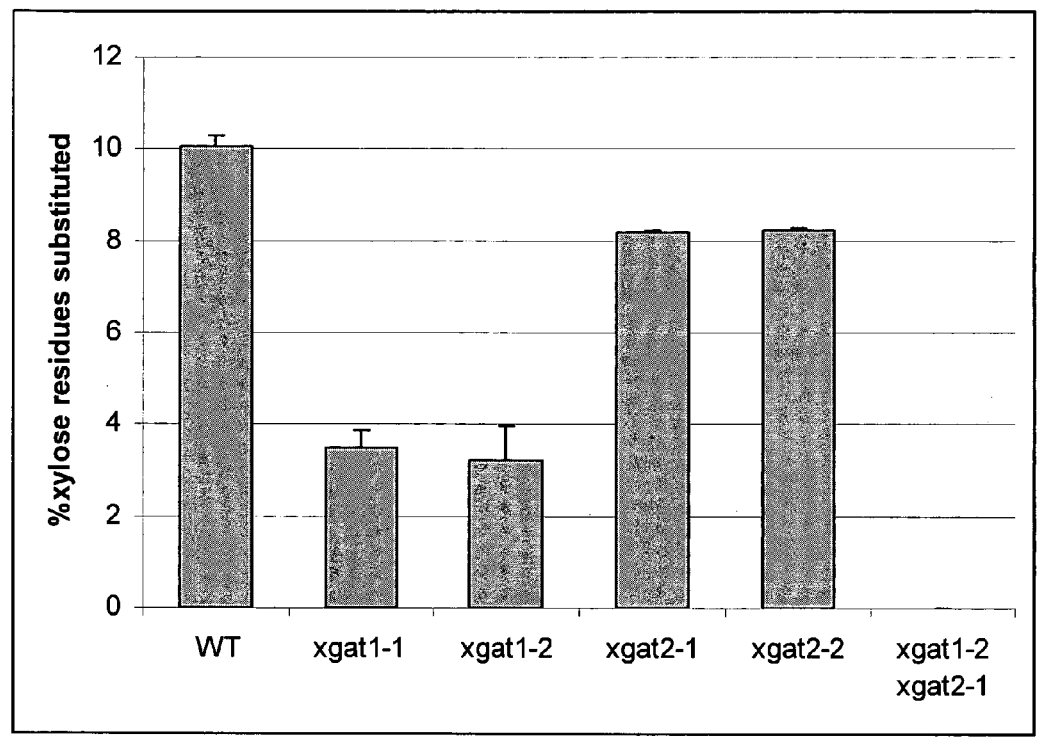

FIG. 3: Substitution of xylose with [Me]GlcA is reduced in xgat1, and missing in xgat1/xgat2 double mutants, as determined by PACE, in two independent experiments (WT n=3).

Figure 4:
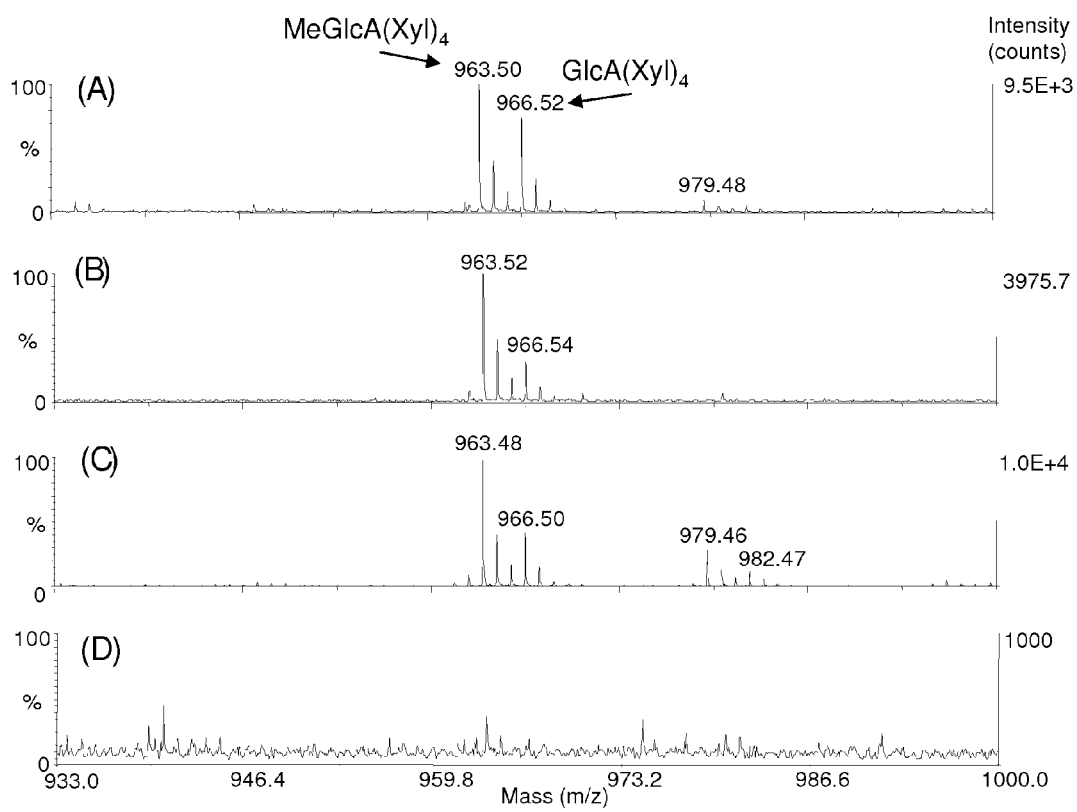

FIG. 4: MALDI-TOF MS of xylanase Xyl11-digested cell walls confirms that $[Me]GlcA(Xyl)_4$ is detected in xgat single mutants, but missing in the double mutant. Both $GlcA(Xyl)_4$ and $[Me]GlcA(Xyl)_4$ are missing in the double mutant. (A) Wild type; (B) xgat1-2; (C) xgat2-1; (D) xgat1-2 xgat2-1.

Figure 5:
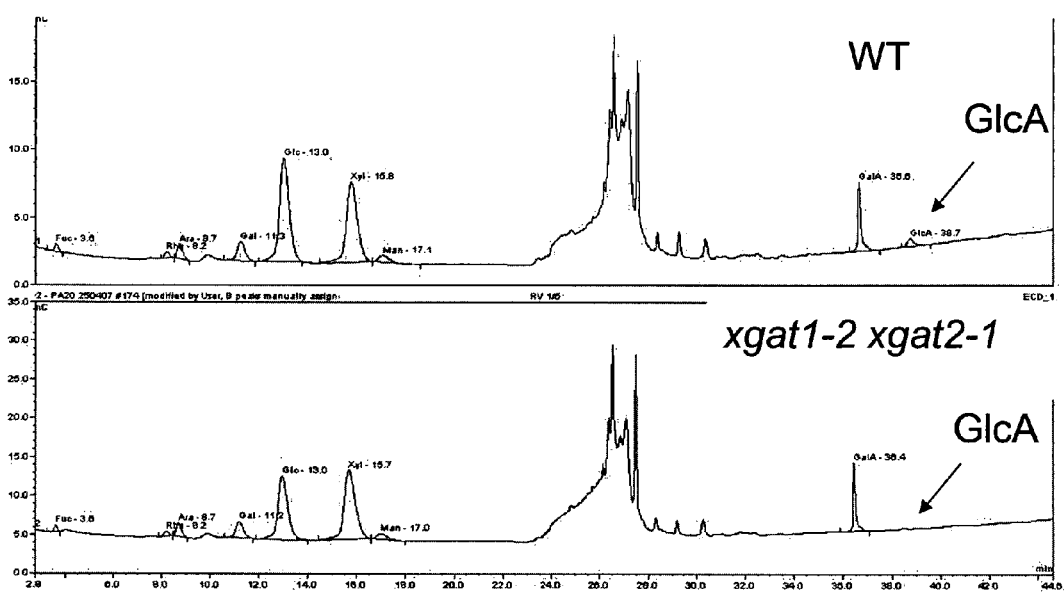

FIG. 5: HPLC analysis of monosaccharides in the depectinated cell wall shows the absence of GlcA in the mutant. Polysaccharides in the walls were hydrolysed by 2 M trifluoroacetic acid at 120° C. for three hours.

Figure 6:
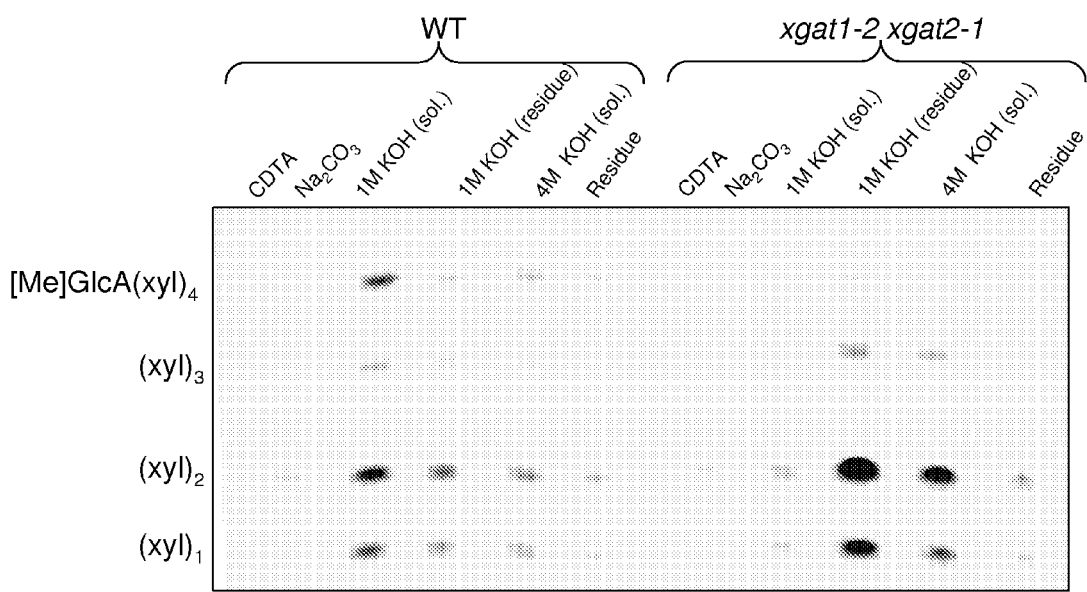

FIG. 6: [Me]GlcA substitution strongly influences the extractability of xylan from walls. Most xylan is extracted by 1M NaOH in the xgat double mutant. Walls were successively extracted by CDTA, Na2CO3, 1M KOH, 4M KOH. The xylan in the extracts and the insoluble residue were then analysed by PACE.

Figure 7:
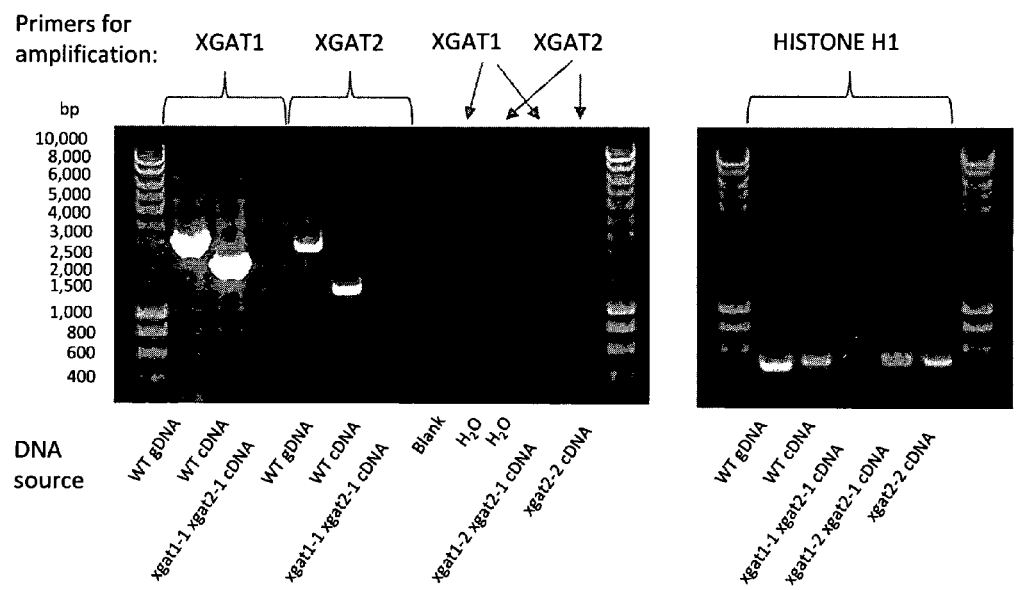

FIG. 7: RT-PCR shows xgat1-1, xgat1-2, xgat2-1 and xgat2-2 are transcriptional knockouts. Histone H1 was used to confirm cDNA quality.

EXAMPLE 1

Analysis of *Arabidopsis thaliana* Plants for the Presence of Insertion in the Genes At4g33330 or At3g18660

To isolate mutant plants lacking the activity of the xgat genes, insertion lines were identified. DNA was extracted and screened by PCR for T-DNA insertions.

*Arabidopsis thaliana* cv Columbia plants of all genotypes were stratified by incubating in water at 4° C. in the dark for 72 hours and subsequently sowed in soil and allowed to grow under controlled environmental conditions (25/20° C., 16-h-light/8-h-dark cycle).

Available T-DNA insertion mutants were identified from the SIGnAL "T-DNA Express" *Arabidopsis* Gene Mapping Tool located in the SIGnAL website.

The following plant insertion lines were identified for the genes of interest, At3g18660 (xgat1) and At4g33330 (xgat2): (xgat1-1, SALK_063763 (NASC stock number N563763); (xgat1-2, SALK_046841 (NASC stock number 546841) and xgat2-1, GK-722F09 (NASC stock number N469285); xgat2-2, SM_3.16768 (NASC stock number N104457).

For DNA extraction, a single rosette leaf from four-week-old plants of all putative T-DNA lines was collected and frozen in liquid nitrogen and ground to a fine powder. The ground leaf tissue was then incubated with pre-heated DNA extraction buffer (20% w/w CTAB, 1.4 M NaCl, 0.02 M EDTA, 0.1 M Tris-HCL pH 8.0) p-mercaptoethanol for 30 min at 60° C. This was followed with chloroform:isoamyl alcohol 24:1 incubation and samples were inverted, centrifuged at 10,000 g for 30 min, and the aqueous layer collected. Cold isopropanol was added, mixed, and subsequently centrifuged at 10,000 g for 30 min and the supernatant removed. The DNA pellets were washed with 70% ethanol, centrifuged at 10,000 g for 5 min, the supernatant was removed, and the DNA re-suspended in DNA suspension buffer (containing 0.1 mM Tris-HCL and 0.02 μM EDTA).

DNA samples representing the various putative mutants were screened for both the wild-type gene and the T-DNA insert. The following primer sets were used to amplify the wild-type gene (open reading frame) of xgat1-1: (R-primer) 5'-CAATGCCGCAGCATACTTTTC-3' (Seq. Id. No. 1) and (L-primer) 5'-GCAAGAGGAGATTCCGGAGAA-3' (Seq. Id. No. 2) (amplification product=2.5 kb) and to amplify the T-DNA insert: (L-primer) 5'-GCAAGAGGAGATTCCG-GAGAA-3' (Seq. Id. No. 2) and (L-border primer) 5'-TTTTTCGCCCTTTGACGTTGGAG-3' (Seq. Id. No. 3) (amplification product=2 kb). xgat1-2: (R-primer) 5'-CAAT-GCCGCAGCATACTTTTC-3' (Seq. Id. No. 1) and (L-primer) 5'-GCAAGAGGAGATTCCGGAGAA-3' (Seq. Id. No. 2) (amplification product=2.5 kb) and to amplify the T-DNA insert: (L-primer) 5'-GCAAGAGGAGATTCCG-GAGAA-3' (Seq. Id. No. 2) and (L-border primer) 5'-TTTTTCGCCCTTTGACGTTGGAG-3' (Seq. Id. No. 3) (amplification product L-border primer/L-primer=0.9 kb). xgat2-1: (R-primer) 5'-TATGATGTCTAAATACAAGGA-3' (Seq. Id. No. 4) and (L-primer) TACGCTTTAATCTAGTCT-TGTT-3' (Seq. Id. No. 5) (amplification product=2.9 kb) and to amplify the T-DNA insert: (R-primer) 5'-TATGAT-GTCTAAATACAAGGA-3' (Seq. Id. No. 4) and (L-border primer2) 5'-ATATTGACCATCATACTCATTGC-3' (Seq. Id. No. 6) (amplification product=0.9 kb). xgat2-2: (R-primer) 5'-TATGATGTCTAAATACAAGGA-3' (Seq. Id. No. 4) and (L-primer) TACGCTTTAATCTAGTCTTGTT-3' (Seq. Id. No. 5) (amplification product=2.9 kb) and to amplify the T-DNA insert: (R-primer) 5'-TATGATGTCTAAATA-CAAGGA-3' (Seq. Id. No. 4) and (L-border primer3) 5'-GGTGCAGCAAAACCCACACTTTTACTTC-3' (Seq. Id. No. 7) (amplification products L-border primer=1.2 kb).

DNA samples (2 µl) were used for PCR reactions and were aliquoted into PCR tubes containing 10 µl Sigma REDTaq ready mix with MgCl$_2$ (Cat #R2523), 1 µl primer (L, R or Left border) adjusted to a final volume of 20 µl using H$_2$O. For loading control and positive control, Histone primers were used in place of the gene/gene or gene/Left border primers. For negative control, 5 µl of sterile water was used instead of DNA. The following PCR program was used with the annealing time adjusted longer or shorter depending on the length of PCR product: 94° C. for 2 min (1 cycle), followed by 94° C. for 15 sec, 55° C. for 30 sec, 68° C. for 3 min (15 cycles), 94° C. for 15 sec, 55° C. sec, 68° C. for 3 min (25 cycles), 68° C. for 10 min (1 cycle), and finally the reaction was held at 4° C. PCR products, 8-10 µl per sample and 5 µl hyperladder, were then loaded onto a 0.8% agarose gel in 1×TAE buffer (0.04 M Tris acetate, 0.001 M EDTA) containing ethidium bromide (5 µl/100 ml). Samples were separated at 100 volts at room temperature for approximately 45 min. The gels were then visualized under UV and imaged using a digital camera.

EXAMPLE 2

Analysis of *Arabidopsis thaliana* Plants for The Presence of Modified Xylan The mutant plants were and for the quantity of [Me]GlcA side chains on the xylan PACE, which involves hydrolysis of the xylan with a xylanase enzyme, derivatisation of oligosaccharides with a fluorophore, and separation of the oligosaccharides by polyacrylamide gel electrophoresis (Goubet at al. 2002).

*Arabidopsis thaliana* plants were grown at 22'C in controlled environment cabinets under a 16 h day light regime of 150 to 180 µmol m$^{-2}$ s$^{-1}$. Stem fractions were incubated for 30 mm in 95% (v/v) ethanol at 65° C. to inactivate enzymes, and then were ground in a Mixer Mill MM200 (Glen Creston, Middlesex, UK). The homogenate was centrifuged at 4,000 g for 15 min. The pellet was washed with 60% (v/v) ethanol (3-4 times), methanol/chloroform (2:3 (v/v); overnight), 100% acetone, ethanol/water [6:4 (v/v)] and ethanol/water [9:1 (v/v)]. The remaining pellet, containing the cell wall, was dried overnight at 80° C.

Dried cell wall material (50 µg) was treated with 4 M NaOH (20 µL) for 1 h at room temperature before adjusting to pH 5-6 with HCl (1 M). The xylan hydrolysis was performed in 0.1 M ammonium acetate pH 6 with 20 mU of xylanase overnight. Endo-β-1, 4-xylanase, Xyl10A (glycosylhydrolase family 10 from *Cellvibrio japonicus*) or Xyl11 (glycosylhydrolase family 11 from *Nocallimastix patriciarum*) was a gift from Harry Gilbert (University of Newcastle, UK), Controls without substrates or enzymes were performed under the same conditions to identify any unspecific compounds in the enzymes, polysaccharides/cell walls or labelling reagents. The reactions were stopped by boiling for 30 min and the samples dried.

Derivatisation of the sugars with ANTS (8-aminonaphtha-lene-1,3,6-trisulfonic acid) was in 10 µL of buffer (DMSO: water:acetic acid, 20:17:3). ANTS was purchased from Molecular Probes (Leiden, The Netherlands). Derivatization was carried out in tubes containing dried polysaccharides, oligosaccharides or monosaccharides. For monosaccharide or oligosaccharide standards, 5 µl of 1 mM sugars were added to a tube and dried before derivatization. ANTS was prepared in acetic acid/water (3/17, v/v) at 0.2 M as final concentration (made freshly or stored at: −20° C.). NaCNBH$_3$ (1 M, made freshly and used immediately) was solubilized in DMS for ANTS derivatisation. To each dry sample 5 µl of ANTS solution and 5 µl of the appropriate NaCNBH$_3$ solution were added. The reagents were mixed, centrifuged, and incubated at 37° C. overnight. The solution was lyophilized in a centrifugal vacuum evaporator for 3 h at 40° C. The derivatised sugars were re-suspended in 100 µL of 3M urea and stored before use at −20° C.

Separation of ANTS-derivatised sugars, using 1 µL of the sample per gel lane, was performed using an Hoefer SE 660 vertical slab gel electrophoresis apparatus (Amersham, Bucks, UK) with 24 cm. plates, 0.75 mm spacer and well of width 0.25 cm. Standard glass or low-fluorescence pyrex plates were used. Electrophoresis was performed at; 10° C. in all cases. The 20% (v/v) polyacrylamide gel contained 0.5% (w/v) N,N'-methylenebisacrylamide with a stacking gel (2 cm) of 8% (w/v) polyacrylamide and 0.2% (w/v) N,N'-methylenebisacrylamide. Polyacrylamide containing a ratio of acrylamide/N,N'-methylenebisacrylamide (29:1) was obtained from Severn Biotech Ltd. (Worcs, UK). The electrophoresis buffer system was 0.1 M Tris adjusted to pH 8.2 with boric acid (Tris-borate). The samples were electrophoresed initially at 200 V for 20 ruin and then at 1,000 V for 90 min.

Gels were scanned using a MasterImager CCD camera system (Amersham, Bucks, UK) with an excitation filter at 400 nm and a detection filter at 530 nm. The exposure time was optimised to increase sensitivity without saturating the intense bands. An image of the gel (resolution, 100 microns) was obtained and exported in a 16 bit file to be quantified. The gel was also visualised using a standard UV transilluminator (wavelength, 360 nm). Quantitation was performed using GeneTools software (Syngene, Cambridge, UK), using rolling ball background detection.

Standards (single or multiple) were run in each gel to obtain a standard curve for quantitating sugars in the samples. Standards for quantification [Xylose, (Man)$_2$ and (Man)$_3$]

were separated alongside samples in each gel to obtain a standard curve of pmol quantity of fluorophore-labelled oligosaccharide. For digests with Xyl11, the quantity of Xyl, $(Xyl)_2$ $(Xyl)_3$ and $[Me]GlcUA(Xyl)_4$ in. 1 ul, of sample was calculated using this standard curve. The ratio of Xyl to Glc/Me-Glc was calculated by summing the relative contribution of the Xyl containing bands=$(Xyl)_1 x1+(Xyl)_2 x2+(Xyl)_3 x3+([Me]GlcUA (Xyl)_4)x4$ compared to GlcUA/MeGlcUA=$([Me]GlcUA(Xyl)_4)x1$.

The structure of the xylan was studied in stems of single mutants, xgat1-2 and xgat2-1 and the double mutant. FIG. 1 snows PACE gels of digests of stem xylan with Xyl11 which yields mostly Xyl, $(Xyl)_2$ $(Xyl)_3$ and $[Me]GlcAXyyl_4$, MeGlcAXyl$_4$ and GlcAXyl$_4$ were not well distinguished by the PACE technique. In the single mutants, the intensity of the $[Me]GlcAXyl_4$ band was reduced. In xgat1-2 xgat2-1 double mutant plant lines, $[Me]GlcAXyl_4$ was absent. The total quantity of xylan backbone was measured in xgat mutants and wild type plants, and found to be identical (FIG. 2). The proportion of xylose residues in the xylan backbone substituted with [Me]GlcA was measured in xgat mutants and wild type plants, and shown to be reduced in the single mutants, and essentially absent in the double mutants (FIG. 3). Together, this indicates that manipulation of XGAT activity can be used to reduce the substitution of xylan by [Me]GlcA, without altering substantially the quantity of xylan.

EXAMPLE 3

Xylan Structure Fingerprinting of Modified Plants by Xylanase Digest Ion and Mass Spectrometry The presence or GlcA or MeGlcA on xylan was investigated by studying xylanase-released oligosaccharides by mass spectrometry.

Cell wall material (500 µg) prepared as Example 2 was treated with 4M NaOH (50 µL) for 1 h at room ten before adjustment to pH. 5-6 with HCl (1M). The xylan hydrolysis was performed in 0.1M ammonium acetate pH6 with 100 mU of xylanase eg Xyl10A or Xyl11 overnight. The reactions were stopped by boiling for 30 min. The samples were filtered using a Nanosep system (molecular weight cut-off of 10 kDa, Pall, New York, USA) and dried. The resulting oligosaccharides were purified using HyperSep Hypercarb cartridges (ThermoHypersil-Keystone, Runcorn, Cheshire, UK) and subsequently analysed by MALDI-TOF-MS. Due to the presence of contaminant signals complicating these native spectra, the remainder of each sample was perdeuteromethylated (using the NaOH slurry method described In Dell et al., 1989) prior to re-analysis by MALDI-TOF-MS All mass spectra were recorded in the positive ion mode on a 4700 Proteomics Analyzer (Applied Biosystems, Foster City, Calif.). This MALDI tandem mass spectrometer uses a 200 Hz frequency-triple Nd-YAG laser operating at a wavelength of 355 nm. 2,5-Dihydroxybenzoic acid (DHB) (Fluka), dissolved in 50% aqueous methanol, was used as the matrix and averages of 2500 shots were used to obtain all MS spectra.

The result of MS analysis of xylanase-released oligosaccharides in xgat single and double mutants is shown (FIG. 4). The 963 and 966 Da [M+Na] corresponds to MeGlcA Xyl$_4$ and GlcAXyl$_4$, respectively and they differ in mass by 3 Da after deuteropermethylation. In the single mutants, both oligosaccharides are still present, but there was a small increase in proportion of MeGlcA Xyl$_4$, over GlcA Xyl$_4$. A much larger increase in proportion of MeGlcA over GlcA has previously been found in xylan synthesis mutants, irx7/fra8, irx3 and irx9 (Pena at al. 2007, Zhong et al., 2005). It can be seen that both MeGlcA and GlcA substitutions disappear in the double mutants, and were not detectable above background. Taken together with the quantitative PACE analysis of substitution level, the MS indicates that manipulation of XGAT activity leads to xylan without [Me] GlcA side chains, and can be used to manipulate both MeGlcA and GlcA substitution of xylan.

EXAMPLE 4

Sugar Composition of Hemicelluloses of Modified *Arabidopsis thaliana* Plants

To detect GlcA in the hemicelluloses, cell walls were prepared as above. Pectin was removed, leaving the hemicelluloses including xylan in the insoluble material ("hemicellulosic material"), Cell wall material (50 µg) was suspended in 1 mL of 0.05 M 1,2-cyclohexanediaminetetraacetic acid (CDTA) (pH 6.5) for 24 h at room temperature. The suspension was centrifuged and the pellet washed once with distilled water. The residue was subsequently extracted using 0.05M $Na_2CO_3$ containing 0.01M $NaBH_4$ for 24 h at 4° C. The residue was adjusted to pH 5 with glacial acetic acid, and then dialysed extensively against de-ionised water for 5 d and then lyophilised.

Hemicellulosic material was acid hydrolysed in 400 µl of 2M trifluoroacetic acid at 120° C. for three hours, dried and suspended in 100 L distilled water.

The monosaccharide analysis was performed a Dionex DX-500 BioLC system composed of an electrochemical detector (ED40), gradient pump (GP50), injector system (IC 30 and UV/VIS detector (UVD 170U), using a CarboPac™ PA20 analytical column (3×150 mm) in combination with a CarboPac™ PA20 guard column (3×30 mm), Dionex Corp., CA, USA, Data was interpreted by Chromeleon software. HPAEC-PAD was performed at 30° C. with a flow rate of 0.5 ml/min using an isocratic gradient of three eluents prepared from deionised water degassed by helium gas: eluent A: 100 mM NaOH, 5.23 ml from 46/48% (w/w) NaOH (Fisher Scientific, UK) stock to minimise the carbonate content; eluent B, 1 M NaOH, 52.3 mL of NaOH stock; eluent D, deionised-degassed water. The column was washed with 200 mM NaOH for 10 min and re-equilibrated with 1.5 mM NaOH for 10 min before the next injection. A 20 µL sample was injected and monitored by pulsed-amperometric detector with a disposable gold working electrode and an $Ag/AgCl_2$ reference electrode (Dionex, CA, USA). GlcA was detected by reference to a standard.

Analysis of wild type and double xgat mutant plants revealed that GlcA was reduced to trace levels in hemicellulose of the modified plants (FIG. 5). This shows that GlcA is missing from the xylan in the modified plants.

EXAMPLE 5

Chemical Extractability of Modified Xylan in *Arabidopsis thaliana*

The quantity of xylan extracted by 0.05 M CDTA (ph 6.5), 1 M NaOH (mild) or 4 M NaOH (strong) base solution was measured by PACE as described in Brown et al (2007).

Dried cell wall material (500 mg) was first extracted with 0.05 M CDTA (pH 6.5) for 24 h at room temperature. The suspension was centrifuged (48 000 g), and the pellet washed once with distilled $H_2O$. The supernatants were combined as the CDTA-soluble fraction. The AIR was subsequently extracted under oxygen-free conditions using 0.05 M Na2CO3 containing 0.01 M NaBH4 for 24 h at 4_C (Na2CO3-soluble fraction), 1 M KOH containing 0.01 M NaBH4 for 24 h at room temperature (1 M KOH-soluble fraction) and then 4 M KOH containing 0.01 M NaBH4 for 24 h at room temperature (4 M KOH soluble fraction). All fractions were filtered through a GF/C glass fibre filter (Whatman). The Na2CO3 and KOH fractions were also chilled on ice and adjusted to pH 5 with glacial acetic acid. All cell-wall fractions were then dialysed extensively against deionized water for 5 days, and then lyophilized The xylan in $1/20^{th}$ of the samples (extract and residue) was hydrolysed in 0.1 M ammonium acetate pH 6 with 20 mU of xylanase overnight. The samples were derivatised with ANTS, and mono- and oligosaccharides were separated polyacrylamide gel electrophoresis as described for Example 2.

In the wild type plants, some of the xylan was solubilised by 1 M NaOH, and some remained attached to the cellulosic residue (FIG. 6). In the xgat double mutant plants, most of the xylan was extracted by 1 M NaOH extraction, in indicating that the interaction with lignin or cellulose in the wall is altered. The absence of the [Me]GlcA in the modified plants improves the extractability of the xylan in mild base solution. This indicates that the manipulation of [Me]GlcA substitution can be used to alter solubility of xylans.

EXAMPLE 6

Xylan Modification in Poplar Species

Xylan is modified in trees such as poplar species by generating transgenic plants with increased expression of XGAT genes, or reduction in XGAT activity using antisense approaches as described herein.

XGAT genes are cloned using primers specific for genes encoding XGATs using procedures as described herein. For poplar, the sequences of PttGTb and pttGT8C are amplified by PCR using cDNAs from hybrid aspen the primers for example:

The text file, "Replacement Sequence Listing Jan 2013" created on Tuesday Jan. 29, 2013, with a size of 76.7 KB and 78,615 Bytes is herein incorporated by reference in its entirety.

PttGT8C, using sequence AY935503,

```
F  5'-GTGCAACCCTTGTTGCTAAGA-3'      (Seq Id No. 8)

R  5'-GCCTCTTTAGTCAAATGAAACAGAAC-3' (Seq Id No. 9)
```

PttGT8B using sequence AY935502 B

```
F  5'-ACGGAAGCGGAAGAAGATAA-3'       (Seq Id No. 10)

R  5'-TCATTTCCCATTAGTCTCACCATAT-3'  (Seq Id No. 11)
```

The sequences are inserted into a cloning vector, such as the pBIN cloning vector under the control of a suitable promoter such as the enhanced tandem CaMV 35S constitutive promoter, or under a promoter specifically active in cells synthesising secondary cell walls, such as the 2 kb of the promoter 5' to an XGAT coding sequence of a dicot plant, such as *Arabidopsis thaliana*. To increase XGAT activity, the sequence is cloned in the sense orientation. To reduce XGAT activity, the sequence is cloned in the reverse (antisense) orientation. The sequence may also be used to generate other constructs that cause the production of double stranded RNA to suppress expression of XGAT genes, using methods well known to those skilled in the art. To confirm the insertion of the promoter and gene into the binary vector, the nucleotide sequence of the construct is determined.

Hybrid poplar is transformed using virulent *Agrobacterium tumefaciens* using standard techniques, such as leaf disc inoculation as described herein. For example, poplar leaf discs are cut and co-cultured with *Agrobacterium tumefaciens* for 1 h at room temperature, blotted dry, and plated abaxially onto suitable agar solidified medium supplemented with 0.1 μM each naphthalene acetic acid (NAA), 6-benzylaminopurine (BA), and thiadiazuron (TDZ). After three days the discs are transferred to agar plates supplemented with carbenicillin disodium (500 mg l$^{-1}$) and cefotaxime sodium salt (250 mg l$^{-1}$). After three further days, the discs are transferred to agar plates with medium containing carbenicillin, cefotaxime, and kanamycin (25 mg l$^{-1}$). After 5 weeks, shoots and callus material are transferred to medium supplemented as above plus 0.01 μM BA. Once individual shoots are visible, plantlets are transferred to solidified medium with 0.01 μM NAA and antibiotic selection to induce rooting. After two consecutive 5-week periods on this medium, shoot tips are isolated to solidified antibiotic-free medium with 0.01 μM NAA.

Plants are confirmed as transformants by PCR screening of genomic DNA employing gene and promoter-specific oligonucleotides as described above.

Plantlets in tissue culture are transferred into 7.5 l pots containing a peat, fine bark, and pumice soil mixture, and grown in a greenhouse until planting in the field.

Clones of plants with improved xylan properties are identified by extracting the xylan with 1M NaOH and comparing the quantity to untransformed plants, or by analysing the xylan branching by PACE as described herein.

References

Goubet, F, P Jackson, M Deery and P Dupree (2002) Polysaccharide Analysis using Carbohydrate gel Electrophoresis (PACE): a method to study plant cell wall polysaccharides and polysaccharide hydrolases. Analytical Biochemistry, 300, 53-68.

The invention claimed is:

1. A transformed plant cell comprising a xylan structure having a non-native [Me]GlcA substitution pattern side chain component, wherein said transformed plant cell comprises an introduced DNA sequence encoding an antisense RNA molecule operably linked to a promoter and a terminator, said promoter and terminator being capable of functioning in a plant cell, wherein said antisense RNA molecule is complementary to a portion of the coding sequence for a xylan glucuronyl transferase (XGAT); or, wherein said transformed plant cell comprises an introduced DNA sequence encoding a sense RNA molecule operably linked to a promoter and a terminator, said promoter and terminator being capable of functioning in a plant cell, wherein said sense RNA molecule is a coding sequence for a xylan glucuronyl transferase (XGAT), and wherein the xylan glucuronyl transferase (XGAT) is a protein selected from the group At4g33330 (SEQ ID NO:12), At3g18660 (SEQ ID NO:13), At1g77130 (SEQ ID NO:14), At1g08990 (SEQ ID NO:15), At1g54940 (SEQ ID NO:16), PttGT8A (SEQ ID NO:17), PttGT8B (SEQ ID NO:18), PttGT8C ((SEQ ID NO:19), CAK29728 ((SEQ ID NO:20), Os03g0184300 (SEQ ID NO:21), Os01g0880200 (SEQ ID NO:22), Os05g0426400 (SEQ ID NO:23), Os1 010047 (SEQ ID NO:24), AAK92624 (SEQ ID NO:25), and ABE88903 ((SEQ ID NO:28) or fragments thereof or a protein encoded by a nucleotide sequence comprising AK250038 (SEQ ID NO:26) or AY110752 (SEQ ID NO:27).

2. A transformed plant cell according to claim 1 wherein the non-native [Me]GlcA substitution side chain component pattern is located on up to 50% of the backbone xylose residues of the xylan structure.

3. A transformed plant cell according to claim 1 that is selected from transformed cells of poplar, loblolly pine, cotton, wheat, barley, rye, sugar beet, miscanthus, willow, switch grass and sugar cane.

4. A method of providing a plant cell comprising a xylan structure having a non-native [Me]GlcA substitution pattern side chain component, the method comprising;
expressing a DNA sequence encoding an antisense RNA molecule operably linked to a promoter and a terminator, said promoter and terminator being capable of functioning in the plant cell,
wherein said antisense RNA molecule is complementary to a portion of the coding sequence for a xylan glucuronyl transferase (XGAT), and
wherein the xylan glucuronyl transferase (XGAT) is a protein selected from the group At4g33330 (SEQ ID NO:12), At3g18660 (SEQ ID NO:13), At1g77130 (SEQ ID NO:14), At1g08990 (SEQ ID NO:15), At1g54940 (SEQ ID NO:16), PttGT8A (SEQ ID NO:17), PttGT8B (SEQ ID NO:18), PttGT8C ((SEQ ID NO:19), CAK29728 ((SEQ ID NO:20), Os03g0184300 (SEQ ID NO:21), Os01g0880200 (SEQ ID NO:22), Os05g0426400 (SEQ ID NO:23), Os1 010047 (SEQ ID NO:24), AAK92624 (SEQ ID NO:25), and ABE88903 ((SEQ ID NO:28) or fragments thereof or a protein encoded by a nucleotide sequence comprising AK250038 (SEQ ID NO:26) or AY110752 (SEQ ID NO:27).

5. A method of providing a plant cell comprising a xylan structure having a non-native [Me]GlcA substitution pattern side chain component, the method comprising:
expressing a DNA sequence encoding a sense RNA molecule operably linked to a promoter and a terminator, said promoter and terminator being capable of functioning in a plant cell,
wherein said sense RNA molecule is a coding sequence for a xylan glucuronyl transferase (XGAT), and
wherein the xylan glucuronyl transferase (XGAT) is a protein selected from the group At4g33330 (SEQ ID NO:12), At3g18660 (SEQ ID NO:13), At1g77130 (SEQ ID NO:14), At1g08990 (SEQ ID NO:15), At1g54940 (SEQ ID NO:16), PttGT8A (SEQ ID NO:17), PttGT8B (SEQ ID NO:18), PttGT8C ((SEQ ID NO:19), CAK29728 ((SEQ ID NO:20), Os03g0184300 (SEQ ID NO:21), Os01g0880200 (SEQ ID NO:22), Os05g0426400 (SEQ ID NO:23), Os1 010047 (SEQ ID NO:24), AAK92624 (SEQ ID NO:25), and ABE88903 ((SEQ ID NO:28) or fragments thereof or a protein encoded by a nucleotide sequence comprising AK250038 (SEQ ID NO:26) or AY110752 (SEQ ID NO:27).

6. A method according to claim 4 wherein the promoter is selected from the group consisting of constitutive, inducible and developmentally regulated promoters.

7. A method according to claim 5 wherein the promoter is selected from the group consisting of constitutive, inducible and developmentally regulated promoters.

8. A method according to claim 6, wherein said nucleotide sequence further comprises a DNA sequence encoding a marker protein, said marker protein being operably linked to a promoter and a terminator, said promoter and terminator functioning in a plant cell.

9. A plant comprising a plant cell according to claim 1.

10. Seed or progeny of the plant according to claim 9, wherein the seed or progeny comprises said plant cell.

11. A plant expressing in its cells an antisense RNA that is complementary to a portion of the coding sequence for a protein having xylan glucuronyl transferase (XGAT) activity:
wherein the xylan glucuronyl transferase (XGAT) is a protein selected from the group At4g33330 (SEQ ID NO:12), At3g18660 (SEQ ID NO:13), At1g77130 (SEQ ID NO:14), At1g08990 (SEQ ID NO:15), At1g54940 (SEQ ID NO:16), PttGT8A (SEQ ID NO:17), PttGT8B (SEQ ID NO:18), PttGT8C ((SEQ ID NO:19), CAK29728 ((SEQ ID NO:20), Os03g0184300 (SEQ ID NO:21), Os01g0880200 (SEQ ID NO:22), Os05g0426400 (SEQ ID NO:23), Os1 010047 (SEQ ID NO:24), AAK92624 (SEQ ID NO:25), and ABE88903 ((SEQ ID NO:28) or fragments thereof or a protein encoded by a nucleotide sequence comprising AK250038 (SEQ ID NO:26) or AY110752

12. A plant according to claim 11 that is derived from transformed cells selected from transformed cells of poplar, loblolly pine, cotton, wheat, barley, rye, sugar beet and sugar cane.

13. An animal feed or animal feed supplement comprising: transformed plant cells comprising a xylan structure having a non-native [Me]GlcA substitution pattern side chain component, said cells being derived from a plant according to claim 9.

14. An animal feed or animal feed supplement comprising: transformed plant cells comprising a xylan structure having a non-native [Me]GlcA substitution pattern side chain component, said cells being derived from a plant according to claim 11.

15. A dietary supplement for human nutrition comprising plant cells according to claim 1.

16. A dietary supplement for human nutrition comprising plant material obtained from a plant according to claim 9.

17. A dietary supplement for human nutrition comprising plant material obtained from a plant according to claim 11.

18. A method for screening plants in a plant population for mutant alleles involved in the [Me]GlcA substitution of xylans that comprises:
i) obtaining nucleic acid samples from the plants;
ii) screening the nucleic acid samples with at least one known marker sequence of an XGAT nucleic acid sequence that is employed in saccharide substitution of xylan;
iii) identifying plants that comprise at least one mutant allele relative to the known marker sequence of step ii), and
wherein the xylan glucuronyl transferase (XGAT) is a protein selected from the group At4g33330 (SEQ ID NO:12), At3g18660 (SEQ ID NO:13), At1g77130 (SEQ ID NO:14), At1g08990 (SEQ ID NO:15), At1g54940 (SEQ ID NO:16), PttGT8A (SEQ ID NO:17), PttGT8B (SEQ ID NO:18), PttGT8C ((SEQ ID NO:19), CAK29728 ((SEQ ID NO:20), Os03g0184300 (SEQ ID NO:21), Os01g0880200 (SEQ ID NO:22), Os05g0426400 (SEQ ID NO:23), Os1 010047 (SEQ ID NO:24), AAK92624 (SEQ ID NO:25), and ABE88903 ((SEQ ID NO:28) or fragments thereof or a protein encoded by a nucleotide sequence comprising AK250038 (SEQ ID NO:26) or AY110752 (SEQ ID NO:27).

19. A method for generating a mutant plant comprising a reduced [Me]GlcA substitution pattern on its xylan structure that comprises:
   i) inserting a DNA sequence into a nucleic acid sequence encoding an xylan glucuronyl transferase (XGAT) into a viable plant cell;
   ii) generating a plant from said plant cell and;
   iii) determining the [Me]GlcA substitution pattern on the xylan structure of said generated plant, and
   wherein the xylan glucuronyl transferase (XGAT) is a protein selected from the group At4g33330 (SEQ ID NO:12), At3g18660 (SEQ ID NO:13), At1g77130 (SEQ ID NO:14), At1g08990 (SEQ ID NO:15), At1g54940 (SEQ ID NO:16), PttGT8A (SEQ ID NO:17), PttGT8B (SEQ ID NO:18), PttGT8C ((SEQ ID NO:19), CAK29728 ((SEQ ID NO:20), Os03g0184300 (SEQ ID NO:21), Os01g0880200 (SEQ ID NO:22), Os05g0426400 (SEQ ID NO:23), Os1 010047 (SEQ ID NO:24), AAK92624 (SEQ ID NO:25), and ABE88903 ((SEQ ID NO:28) or fragments thereof or a protein encoded by a nucleotide sequence comprising AK250038 (SEQ ID NO:26) or AY110752 (SEQ ID NO:27).

20. A method according to claim 19 wherein the inserted nucleic acid is a T-DNA nucleic acid sequence or a nonsense nucleic acid sequence.

21. A method according to claim 7, wherein said nucleotide sequence further comprises a DNA sequence encoding a marker protein, said marker protein being operably linked to a promoter and a terminator, said promoter and terminator functioning in a plant cell.

22. A transformed plant cell comprising a xylan structure having a non-native [Me]GlcA substitution pattern side chain component,
   wherein said transformed plant cell comprises an introduced DNA sequence encoding an antisense RNA molecule operably linked to a promoter and a terminator, said promoter and tetininator being capable of functioning in a plant cell, wherein said antisense RNA molecule is complementary to a portion of the coding sequence for a xylan glucuronyl transferase (XGAT); or,
   wherein said transformed plant cell comprises an introduced DNA sequence encoding a sense RNA molecule operably linked to a promoter and a terminator, said promoter and terminator being capable of functioning in a plant cell, wherein said sense RNA molecule is a coding sequence for a xylan glucuronyl transferase (XGAT), and
   wherein the RNA molecule hybridises to a sequence encoding At4g33330 (SEQ ID NO:12) under stringent conditions, wherein said conditions comprise hybridisation at 50-70° C. in 2×SSC and washing at 1×SSC.

* * * * *

SEQUENCE LISTING

<160> NUMBER OF SEQ ID NOS: 28

<210> SEQ ID NO 1
<211> LENGTH: 21
<212> TYPE: DNA
<213> ORGANISM: Artificial sequence
<220> FEATURE:
<223> OTHER INFORMATION: Synthetic sequence: Primer -continued

```
<400> SEQUENCE: 1
caatgccgca gcatactttt c                                              21

<210> SEQ ID NO 2
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 2
gcaagaggag attccggaga a                                              21

<210> SEQ ID NO 3
<211> LENGTH: 23
<212> TYPE: DNA
<213> ORGANISM: Artificial sequence
<220> FEATURE:
<223> OTHER INFORMATION: Synthetic sequence: Primer

<400> SEQUENCE: 3
tttttcgccc tttgacgttg gag                                            23

<210> SEQ ID NO 4
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 4
tatgatgtct aaatacaagg a                                              21

<210> SEQ ID NO 5
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 5
tacgctttaa tctagtcttg tt                                             22

<210> SEQ ID NO 6
<211> LENGTH: 23
<212> TYPE: DNA
<213> ORGANISM: Artificial sequence
<220> FEATURE:
<223> OTHER INFORMATION: Synthetic sequence: Primer

<400> SEQUENCE: 6
atattgacca tcatactcat tgc                                            23

<210> SEQ ID NO 7
<211> LENGTH: 28
<212> TYPE: DNA
<213> ORGANISM: Artificial sequence
<220> FEATURE:
<223> OTHER INFORMATION: Synthetic sequence: Primer

<400> SEQUENCE: 7
ggtgcagcaa aacccacact tttacttc                                       28

<210> SEQ ID NO 8
<211> LENGTH: 21
```

```
<212> TYPE: DNA
<213> ORGANISM: Artificial sequence
<220> FEATURE:
<223> OTHER INFORMATION: Synthetic sequence: Primer

<400> SEQUENCE: 8
gtgcaaccct tgttgctaag a                                              21

<210> SEQ ID NO 9
<211> LENGTH: 26
<212> TYPE: DNA
<213> ORGANISM: Artificial sequence
<220> FEATURE:
<223> OTHER INFORMATION: Synthetic sequence: Primer

<400> SEQUENCE: 9
gcctctttag tcaaatgaaa cagaac                                         26

<210> SEQ ID NO 10
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 10
acggaagcgg aagaagataa                                                20

<210> SEQ ID NO 11
<211> LENGTH: 25
<212> TYPE: DNA
<213> ORGANISM: Artificial sequence
<220> FEATURE:
<223> OTHER INFORMATION: Synthetic sequence: Primer

<400> SEQUENCE: 11
tcatttccca ttagtctcac catat                                          25

<210> SEQ ID NO 12
<211> LENGTH: 596
<212> TYPE: PRT
<213> ORGANISM: Arabidopsis thaliana

<400> SEQUENCE: 12
```

Met Thr Ile Met Thr Met Ile Met Lys Met Ala Pro Ser Lys Ser Ala
1               5                   10                  15

Leu Ile Arg Phe Asn Leu Val Leu Leu Gly Phe Ser Phe Leu Leu Tyr
            20                  25                  30

Thr Ala Ile Phe Phe His Pro Ser Ser Ser Val Tyr Phe Ser Ser Gly
        35                  40                  45

Ala Ser Phe Val Gly Cys Ser Phe Arg Asp Cys Thr Pro Lys Val Val
    50                  55                  60

Arg Gly Val Lys Met Gln Glu Leu Val Glu Glu Asn Glu Ile Asn Lys
65                  70                  75                  80

Lys Asp Leu Leu Thr Ala Ser Asn Gln Thr Lys Leu Glu Ala Pro Ser
                85                  90                  95

Phe Met Glu Glu Ile Leu Thr Arg Gly Leu Gly Lys Thr Lys Ile Gly
            100                 105                 110

Met Val Asn Met Glu Glu Cys Asp Leu Thr Asn Trp Lys Arg Tyr Gly
        115                 120                 125

Glu Thr Val His Ile His Phe Glu Arg Val Ser Lys Leu Phe Lys Trp
    130                 135                 140

```
Gln Asp Leu Phe Pro Glu Trp Ile Asp Glu Glu Glu Thr Glu Val
145                 150                 155                 160

Pro Thr Cys Pro Glu Ile Pro Met Pro Asp Phe Glu Ser Leu Glu Lys
                165                 170                 175

Leu Asp Leu Val Val Lys Leu Pro Cys Asn Tyr Pro Glu Glu Gly
                180                 185                 190

Trp Arg Arg Glu Val Leu Arg Leu Gln Val Asn Leu Val Ala Ala Asn
            195                 200                 205

Leu Ala Ala Lys Lys Gly Lys Thr Asp Trp Arg Trp Lys Ser Lys Val
210                 215                 220

Leu Phe Trp Ser Lys Cys Gln Pro Met Ile Glu Ile Phe Arg Cys Asp
225                 230                 235                 240

Asp Leu Glu Lys Arg Glu Ala Asp Trp Trp Leu Tyr Arg Pro Glu Val
                245                 250                 255

Val Arg Leu Gln Gln Arg Leu Ser Leu Pro Val Gly Ser Cys Asn Leu
                260                 265                 270

Ala Leu Pro Leu Trp Ala Pro Gln Gly Val Asp Lys Val Tyr Asp Leu
                275                 280                 285

Thr Lys Ile Glu Ala Glu Thr Lys Arg Pro Lys Arg Glu Ala Tyr Val
290                 295                 300

Thr Val Leu His Ser Ser Glu Ser Tyr Val Cys Gly Ala Ile Thr Leu
305                 310                 315                 320

Ala Gln Ser Leu Leu Gln Thr Asn Thr Lys Arg Asp Leu Ile Leu Leu
                325                 330                 335

His Asp Asp Ser Ile Ser Ile Thr Lys Leu Arg Ala Leu Ala Ala Ala
                340                 345                 350

Gly Trp Lys Leu Arg Arg Ile Ile Arg Ile Arg Asn Pro Leu Ala Glu
                355                 360                 365

Lys Asp Ser Tyr Asn Glu Tyr Asn Tyr Ser Lys Phe Arg Leu Trp Gln
                370                 375                 380

Leu Thr Asp Tyr Asp Lys Val Ile Phe Ile Asp Ala Asp Ile Ile Val
385                 390                 395                 400

Leu Arg Asn Leu Asp Leu Leu Phe His Phe Pro Gln Met Ser Ala Thr
                405                 410                 415

Gly Asn Asp Val Trp Ile Tyr Asn Ser Gly Ile Met Val Ile Glu Pro
                420                 425                 430

Ser Asn Cys Thr Phe Thr Thr Ile Met Ser Gln Arg Ser Glu Ile Val
                435                 440                 445

Ser Tyr Asn Gly Gly Asp Gln Gly Tyr Leu Asn Glu Ile Phe Val Trp
                450                 455                 460

Trp His Arg Leu Pro Arg Arg Val Asn Phe Leu Lys Asn Phe Trp Ser
465                 470                 475                 480

Asn Thr Thr Lys Glu Arg Asn Ile Lys Asn Asn Leu Phe Ala Ala Glu
                485                 490                 495

Pro Pro Gln Val Tyr Ala Val His Tyr Leu Gly Trp Lys Pro Trp Leu
                500                 505                 510

Cys Tyr Arg Asp Tyr Asp Cys Asn Tyr Asp Val Asp Glu Gln Leu Val
                515                 520                 525

Tyr Ala Ser Asp Ala Ala His Val Arg Trp Trp Lys Val His Asp Ser
                530                 535                 540

Met Asp Asp Ala Leu Gln Lys Phe Cys Arg Leu Thr Lys Lys Arg Arg
545                 550                 555                 560
```

```
Thr Glu Ile Asn Trp Glu Arg Arg Lys Ala Arg Leu Arg Gly Ser Thr
                    565                 570                 575
Asp Tyr His Trp Lys Ile Asn Val Thr Asp Pro Arg Arg Arg Ser
            580                 585                 590
Tyr Leu Ile Gly
        595

<210> SEQ ID NO 13
<211> LENGTH: 659
<212> TYPE: PRT
<213> ORGANISM: Arabidopsis thaliana

<400> SEQUENCE: 13

Met Ala Asn Ser Pro Ala Ala Pro Ala Pro Thr Thr Thr Gly Gly
1               5                   10                  15
Asp Ser Arg Arg Arg Leu Ser Ala Ser Ile Glu Ala Ile Cys Lys Arg
                20                  25                  30
Arg Phe Arg Arg Asn Ser Lys Gly Gly Gly Arg Ser Asp Met Val Lys
            35                  40                  45
Pro Phe Asn Ile Ile Asn Phe Ser Thr Gln Asp Lys Asn Ser Ser Cys
50                  55                  60
Cys Cys Phe Thr Lys Phe Gln Ile Val Lys Leu Leu Leu Phe Ile Leu
65                  70                  75                  80
Leu Ser Ala Thr Leu Phe Thr Ile Ile Tyr Ser Pro Glu Ala Tyr His
                85                  90                  95
His Ser Leu Ser His Ser Ser Ser Arg Trp Ile Trp Arg Arg Gln Asp
            100                 105                 110
Pro Arg Tyr Phe Ser Asp Leu Asp Ile Asn Trp Asp Val Thr Lys
        115                 120                 125
Thr Leu Glu Asn Ile Glu Glu Gly Arg Thr Ile Gly Val Leu Asn Phe
    130                 135                 140
Asp Ser Asn Glu Ile Gln Arg Trp Arg Glu Val Ser Lys Ser Lys Asp
145                 150                 155                 160
Asn Gly Asp Glu Glu Lys Val Val Val Leu Asn Leu Asp Tyr Ala Asp
                165                 170                 175
Lys Asn Val Thr Trp Asp Ala Leu Tyr Pro Glu Trp Ile Asp Glu Glu
            180                 185                 190
Gln Glu Thr Glu Val Pro Val Cys Pro Asn Ile Pro Asn Ile Lys Val
        195                 200                 205
Pro Thr Arg Arg Leu Asp Leu Ile Val Val Lys Leu Pro Cys Arg Lys
    210                 215                 220
Glu Gly Asn Trp Ser Arg Asp Val Gly Arg Leu His Leu Gln Leu Ala
225                 230                 235                 240
Ala Ala Thr Val Ala Ala Ser Ala Lys Gly Phe Phe Arg Gly His Val
                245                 250                 255
Phe Phe Val Ser Arg Cys Phe Pro Ile Pro Asn Leu Phe Arg Cys Lys
            260                 265                 270
Asp Leu Val Ser Arg Arg Gly Asp Val Trp Leu Tyr Lys Pro Asn Leu
        275                 280                 285
Asp Thr Leu Arg Asp Lys Leu Gln Leu Pro Val Gly Ser Cys Glu Leu
    290                 295                 300
Ser Leu Pro Leu Gly Ile Gln Asp Arg Pro Ser Leu Gly Asn Pro Lys
305                 310                 315                 320
Arg Glu Ala Tyr Ala Thr Ile Leu His Ser Ala His Val Tyr Val Cys
                325                 330                 335
```

Gly Ala Ile Ala Ala Ala Gln Ser Ile Arg Gln Ser Gly Ser Thr Arg
                340                 345                 350

Asp Leu Val Ile Leu Val Asp Asn Ile Ser Gly Tyr His Arg Ser
            355                 360                 365

Gly Leu Glu Ala Ala Gly Trp Gln Ile Arg Thr Ile Gln Arg Ile Arg
        370                 375                 380

Asn Pro Lys Ala Glu Lys Asp Ala Tyr Asn Glu Trp Asn Tyr Ser Lys
385                 390                 395                 400

Phe Arg Leu Trp Gln Leu Thr Asp Tyr Asp Lys Ile Ile Phe Ile Asp
                405                 410                 415

Ala Asp Leu Leu Ile Leu Arg Asn Ile Asp Phe Leu Phe Ser Met Pro
            420                 425                 430

Glu Ile Ser Ala Thr Gly Asn Asn Gly Thr Leu Phe Asn Ser Gly Val
        435                 440                 445

Met Val Ile Glu Pro Cys Asn Cys Thr Phe Gln Leu Leu Met Glu His
            450                 455                 460

Ile Asn Glu Ile Glu Ser Tyr Asn Gly Gly Asp Gln Gly Tyr Leu Asn
465                 470                 475                 480

Glu Val Phe Thr Trp Trp His Arg Ile Pro Lys His Met Asn Phe Leu
                485                 490                 495

Lys His Phe Trp Ile Gly Asp Glu Asp Asp Ala Lys Arg Lys Lys Thr
            500                 505                 510

Glu Leu Phe Gly Ala Glu Pro Pro Val Leu Tyr Val Leu His Tyr Leu
        515                 520                 525

Gly Met Lys Pro Trp Leu Cys Tyr Arg Asp Tyr Asp Cys Asn Phe Asn
            530                 535                 540

Ser Asp Ile Phe Val Glu Phe Ala Thr Asp Ile Ala His Arg Lys Trp
545                 550                 555                 560

Trp Met Val His Asp Ala Met Pro Gln Glu Leu His Gln Phe Cys Tyr
                565                 570                 575

Leu Arg Ser Lys Gln Lys Ala Gln Leu Glu Tyr Asp Arg Arg Gln Ala
            580                 585                 590

Glu Ala Ala Asn Tyr Ala Asp Gly His Trp Lys Ile Arg Val Lys Asp
        595                 600                 605

Pro Arg Phe Lys Ile Cys Ile Asp Lys Leu Cys Asn Trp Lys Ser Met
            610                 615                 620

Leu Arg His Trp Gly Glu Ser Asn Trp Thr Asp Tyr Glu Ser Phe Val
625                 630                 635                 640

Pro Thr Pro Pro Ala Ile Thr Val Asp Arg Arg Ser Ser Leu Pro Gly
                645                 650                 655

His Asn Leu

<210> SEQ ID NO 14
<211> LENGTH: 618
<212> TYPE: PRT
<213> ORGANISM: Arabidopsis thaliana

<400> SEQUENCE: 14

Met Ile Pro Ser Ser Pro Met Glu Ser Arg His Arg Leu Ser Phe
1               5                   10                  15

Ser Asn Glu Lys Thr Ser Arg Arg Phe Gln Arg Ile Glu Lys Gly
            20                  25                  30

Val Lys Phe Asn Thr Leu Lys Leu Val Leu Ile Cys Ile Met Leu Gly
        35                  40                  45

```
Ala Leu Phe Thr Ile Tyr Arg Phe Arg Tyr Pro Pro Leu Gln Ile Pro
    50                  55                  60

Glu Ile Pro Thr Ser Phe Gly Leu Thr Thr Asp Pro Arg Tyr Val Ala
 65                  70                  75                  80

Thr Ala Glu Ile Asn Trp Asn His Met Ser Asn Leu Val Glu Lys His
                 85                  90                  95

Val Phe Gly Arg Ser Glu Tyr Gln Gly Ile Gly Leu Ile Asn Leu Asn
                100                 105                 110

Asp Asn Glu Ile Asp Arg Phe Lys Glu Val Thr Lys Ser Asp Cys Asp
            115                 120                 125

His Val Ala Leu His Leu Asp Tyr Ala Ala Lys Asn Ile Thr Trp Glu
    130                 135                 140

Ser Leu Tyr Pro Glu Trp Ile Asp Glu Val Glu Glu Phe Glu Val Pro
145                 150                 155                 160

Thr Cys Pro Ser Leu Pro Leu Ile Gln Ile Pro Gly Lys Pro Arg Ile
                165                 170                 175

Asp Leu Val Ile Ala Lys Leu Pro Cys Asp Lys Ser Gly Lys Trp Ser
                180                 185                 190

Arg Asp Val Ala Arg Leu His Leu Gln Leu Ala Ala Arg Val Ala
            195                 200                 205

Ala Ser Ser Lys Gly Leu His Asn Val His Val Ile Leu Val Ser Asp
    210                 215                 220

Cys Phe Pro Ile Pro Asn Leu Phe Thr Gly Gln Glu Leu Val Ala Arg
225                 230                 235                 240

Gln Gly Asn Ile Trp Leu Tyr Lys Pro Asn Leu His Gln Leu Arg Gln
                245                 250                 255

Lys Leu Gln Leu Pro Val Gly Ser Cys Glu Leu Ser Val Pro Leu Gln
            260                 265                 270

Ala Lys Asp Asn Phe Tyr Ser Ala Gly Ala Lys Lys Glu Ala Tyr Ala
    275                 280                 285

Thr Ile Leu His Ser Ala Gln Phe Tyr Val Cys Gly Ala Ile Ala Ala
    290                 295                 300

Ala Gln Ser Ile Arg Met Ser Gly Ser Thr Arg Asp Leu Val Ile Leu
305                 310                 315                 320

Val Asp Glu Thr Ile Ser Glu Tyr His Lys Ser Gly Leu Val Ala Ala
                325                 330                 335

Gly Trp Lys Ile Gln Met Phe Gln Arg Ile Arg Asn Pro Asn Ala Val
            340                 345                 350

Pro Asn Ala Tyr Asn Glu Trp Asn Tyr Ser Lys Phe Arg Leu Trp Gln
    355                 360                 365

Leu Thr Glu Tyr Ser Lys Ile Ile Phe Ile Asp Ala Asp Met Leu Ile
    370                 375                 380

Leu Arg Asn Ile Asp Phe Leu Phe Glu Phe Pro Glu Ile Ser Ala Thr
385                 390                 395                 400

Gly Asn Asn Ala Thr Leu Phe Asn Ser Gly Leu Met Val Val Glu Pro
                405                 410                 415

Ser Asn Ser Thr Phe Gln Leu Leu Met Asp Asn Ile Asn Glu Val Val
            420                 425                 430

Ser Tyr Asn Gly Gly Asp Gln Gly Tyr Leu Asn Glu Ile Phe Thr Trp
    435                 440                 445

Trp His Arg Ile Pro Lys His Met Asn Phe Leu Lys His Phe Trp Glu
450                 455                 460
```

```
Gly Asp Glu Pro Glu Ile Lys Lys Met Lys Thr Ser Leu Phe Gly Ala
465                 470                 475                 480

Asp Pro Pro Ile Leu Tyr Val Leu His Tyr Leu Gly Tyr Asn Lys Pro
            485                 490                 495

Trp Leu Cys Phe Arg Asp Tyr Asp Cys Asn Trp Asn Val Asp Ile Phe
        500                 505                 510

Gln Glu Phe Ala Ser Asp Gly Ala His Lys Thr Trp Trp Arg Val His
        515                 520                 525

Asp Ala Met Pro Glu Asn Leu His Lys Phe Cys Leu Leu Arg Ser Lys
        530                 535                 540

Gln Lys Ala Gln Leu Glu Trp Asp Arg Arg Gln Ala Glu Lys Gly Asn
545                 550                 555                 560

Tyr Lys Asp Gly His Trp Lys Ile Lys Ile Lys Asp Lys Arg Leu Lys
                565                 570                 575

Thr Cys Phe Glu Asp Phe Cys Phe Trp Glu Ser Met Leu Trp His Trp
            580                 585                 590

Gly Glu Thr Asn Ser Thr Asn Asn Ser Ser Thr Thr Thr Thr Ser Ser
                595                 600                 605

Pro Pro His Lys Thr Ala Leu Pro Ser Leu
    610                 615

<210> SEQ ID NO 15
<211> LENGTH: 424
<212> TYPE: PRT
<213> ORGANISM: Arabidopsis thaliana

<400> SEQUENCE: 15

Met Glu Gly Ser Glu Ala Asp Val Asp Val Val Val Lys Val Pro
1               5                   10                  15

Cys Asp Gly Phe Ser Glu Lys Arg Gly Leu Arg Asp Val Phe Arg Leu
            20                  25                  30

Gln Val Asn Leu Ala Ala Ala Asn Leu Val Val Glu Ser Gly Arg Arg
        35                  40                  45

Asn Val Asp Arg Thr Val Tyr Val Val Phe Ile Gly Ser Cys Gly Pro
50                  55                  60

Met His Glu Ile Phe Arg Cys Asp Glu Arg Val Lys Arg Val Gly Asp
65                  70                  75                  80

Tyr Trp Val Tyr Arg Pro Asp Leu Thr Arg Leu Lys Gln Lys Leu Leu
                85                  90                  95

Met Pro Pro Gly Ser Cys Gln Ile Ala Pro Leu Gly Gln Gly Glu Ala
            100                 105                 110

Trp Ile Gln Asp Lys Asn Arg Asn Leu Thr Ser Glu Lys Thr Thr Leu
        115                 120                 125

Ser Ser Phe Thr Ala Gln Arg Val Ala Tyr Val Thr Leu Leu His Ser
    130                 135                 140

Ser Glu Val Tyr Val Cys Gly Ala Ile Ala Leu Ala Gln Ser Ile Arg
145                 150                 155                 160

Gln Ser Gly Ser Thr Lys Asp Met Ile Leu Leu His Asp Asp Ser Ile
                165                 170                 175

Thr Asn Ile Ser Leu Ile Gly Leu Ser Leu Ala Gly Trp Lys Leu Arg
            180                 185                 190

Arg Val Glu Arg Ile Arg Ser Pro Phe Ser Lys Lys Arg Ser Tyr Asn
        195                 200                 205

Glu Trp Asn Tyr Ser Lys Leu Arg Val Trp Gln Val Thr Asp Tyr Asp
    210                 215                 220
```

```
Lys Leu Val Phe Ile Asp Ala Asp Phe Ile Ile Val Lys Asn Ile Asp
225                 230                 235                 240

Tyr Leu Phe Ser Tyr Pro Gln Leu Ser Ala Gly Asn Asn Lys Val
            245                 250                 255

Leu Phe Asn Ser Gly Val Met Val Leu Glu Pro Ser Ala Cys Leu Phe
            260                 265                 270

Glu Asp Leu Met Leu Lys Ser Phe Lys Ile Gly Ser Tyr Asn Gly Gly
            275                 280                 285

Asp Gln Gly Phe Leu Asn Glu Tyr Phe Val Trp Trp His Arg Leu Ser
            290                 295                 300

Lys Arg Leu Asn Thr Met Lys Tyr Phe Gly Asp Glu Ser Arg His Asp
305                 310                 315                 320

Lys Ala Arg Asn Leu Pro Glu Asn Leu Glu Gly Ile His Tyr Leu Gly
                325                 330                 335

Leu Lys Pro Trp Arg Cys Tyr Arg Asp Tyr Asp Cys Asn Trp Asp Leu
            340                 345                 350

Lys Thr Arg Arg Val Tyr Ala Ser Glu Ser Val His Ala Arg Trp Trp
            355                 360                 365

Lys Val Tyr Asp Lys Met Pro Lys Lys Leu Lys Gly Tyr Cys Gly Leu
            370                 375                 380

Asn Leu Lys Met Glu Lys Asn Val Glu Lys Trp Arg Lys Met Ala Lys
385                 390                 395                 400

Leu Asn Gly Phe Pro Glu Asn His Trp Lys Ile Arg Ile Lys Asp Pro
                405                 410                 415

Arg Lys Lys Asn Arg Leu Ser Gln
            420

<210> SEQ ID NO 16
<211> LENGTH: 557
<212> TYPE: PRT
<213> ORGANISM: Arabidopsis thaliana

<400> SEQUENCE: 16

Met Gly Thr Lys Thr His Asn Ser Arg Gly Lys Ile Phe Met Ile Tyr
1               5                   10                  15

Leu Ile Leu Val Ser Leu Ser Leu Leu Gly Leu Ile Leu Pro Phe Lys
            20                  25                  30

Pro Leu Phe Arg Ile Thr Ser Pro Ser Ser Thr Leu Arg Ile Asp Leu
            35                  40                  45

Pro Ser Pro Gln Val Asn Lys Asn Pro Lys Trp Leu Arg Leu Ile Arg
        50                  55                  60

Asn Tyr Leu Pro Glu Lys Arg Ile Gln Val Gly Phe Leu Asn Ile Asp
65                  70                  75                  80

Glu Lys Glu Arg Glu Ser Tyr Glu Ala Arg Gly Pro Leu Val Leu Lys
                85                  90                  95

Asn Ile His Val Pro Leu Asp His Ile Pro Lys Asn Val Thr Trp Lys
            100                 105                 110

Ser Leu Tyr Pro Glu Trp Ile Asn Glu Glu Ala Ser Thr Cys Pro Glu
            115                 120                 125

Ile Pro Leu Pro Gln Pro Glu Gly Ser Asp Ala Asn Val Asp Val Ile
            130                 135                 140

Val Ala Arg Val Pro Cys Asp Gly Trp Ser Ala Asn Lys Gly Leu Arg
145                 150                 155                 160

Asp Val Phe Arg Leu Gln Val Asn Leu Ala Ala Ala Asn Leu Ala Val
```

```
                   165                 170                 175
Gln Ser Gly Leu Arg Thr Val Asn Gln Ala Val Tyr Val Phe Ile
        180                 185                 190
Gly Ser Cys Gly Pro Met His Glu Ile Phe Pro Cys Asp Glu Arg Val
        195                 200                 205
Met Arg Val Glu Asp Tyr Trp Val Tyr Lys Pro Tyr Leu Pro Arg Leu
        210                 215                 220
Lys Gln Lys Leu Leu Met Pro Val Gly Ser Cys Gln Ile Ala Pro Ser
225                 230                 235                 240
Phe Ala Gln Phe Gly Gln Glu Ala Trp Arg Pro Lys His Glu Asp Asn
                245                 250                 255
Leu Ala Ser Lys Ala Val Thr Ala Leu Pro Arg Arg Leu Arg Val Ala
            260                 265                 270
Tyr Val Thr Val Leu His Ser Ser Glu Ala Tyr Val Cys Gly Ala Ile
        275                 280                 285
Ala Leu Ala Gln Ser Ile Arg Gln Ser Gly Ser His Lys Asp Met Ile
        290                 295                 300
Leu Leu His Asp His Thr Ile Thr Asn Lys Ser Leu Ile Gly Leu Ser
305                 310                 315                 320
Ala Ala Gly Trp Asn Leu Arg Leu Ile Asp Arg Ile Arg Ser Pro Phe
                325                 330                 335
Ser Gln Lys Asp Ser Tyr Asn Glu Trp Asn Tyr Ser Lys Leu Arg Val
            340                 345                 350
Trp Gln Val Thr Asp Tyr Asp Lys Leu Val Phe Ile Asp Ala Asp Phe
        355                 360                 365
Ile Ile Leu Lys Lys Leu Asp His Leu Phe Tyr Tyr Pro Gln Leu Ser
370                 375                 380
Ala Ser Gly Asn Asp Lys Val Leu Phe Asn Ser Gly Ile Met Val Leu
385                 390                 395                 400
Glu Pro Ser Ala Cys Met Phe Lys Asp Leu Met Glu Lys Ser Phe Lys
                405                 410                 415
Ile Glu Ser Tyr Asn Gly Gly Asp Gln Gly Phe Leu Asn Glu Ile Phe
            420                 425                 430
Val Trp Trp His Arg Leu Ser Lys Arg Val Asn Thr Met Lys Tyr Phe
        435                 440                 445
Asp Glu Lys Asn His Arg Arg His Asp Leu Pro Glu Asn Val Glu Gly
        450                 455                 460
Leu His Tyr Leu Gly Leu Lys Pro Trp Val Cys Tyr Arg Asp Tyr Asp
465                 470                 475                 480
Cys Asn Trp Asp Ile Ser Glu Arg Arg Val Phe Ala Ser Asp Ser Val
                485                 490                 495
His Glu Lys Trp Trp Lys Val Tyr Asp Lys Met Ser Glu Gln Leu Lys
            500                 505                 510
Gly Tyr Cys Gly Leu Asn Lys Asn Met Glu Lys Arg Ile Glu Lys Trp
        515                 520                 525
Arg Arg Ile Ala Lys Asn Asn Ser Leu Pro Asp Arg His Trp Glu Ile
        530                 535                 540
Glu Val Arg Asp Pro Arg Lys Thr Asn Leu Leu Val Gln
545                 550                 555

<210> SEQ ID NO 17
<211> LENGTH: 360
<212> TYPE: PRT
<213> ORGANISM: Populus trichocarpa
```

<400> SEQUENCE: 17

```
Met Leu Glu Leu Phe Arg Cys Asp Asp Leu Val Lys Gln Gly Asp
1               5                   10                  15

Trp Trp Phe Tyr Glu Pro Glu Met Thr Lys Leu Glu Gln Lys Val Ser
            20                  25                  30

Leu Pro Ile Gly Ser Cys Lys Leu Ala Leu Pro Leu Trp Thr Gln Gly
            35                  40                  45

Ile Asn Glu Val Tyr Asp Leu Ser Lys Ile Gln Arg Thr Thr Arg Thr
50                  55                  60

Thr Lys Arg Glu Ala Tyr Ala Thr Val Leu His Ser Ser Glu Ala Tyr
65                  70                  75                  80

Val Cys Gly Val Ile Ala Leu Ala Gln Ser Leu Leu Gln Thr Gly Thr
                85                  90                  95

Lys Arg Asp Leu Val Leu Leu Asp Asn Ser Ile Ser Glu Pro Lys
            100                 105                 110

Arg His Ala Leu Ala Ala Ala Gly Trp Lys Ile Arg Leu Ile Lys Arg
            115                 120                 125

Ile Arg Asn Pro Arg Ala Glu Lys Tyr Ser Tyr Asn Glu Tyr Asn Tyr
130                 135                 140

Ser Lys Phe Arg Leu Trp Gln Leu Thr Asp Tyr Asp Lys Ile Val Phe
145                 150                 155                 160

Ile Asp Ala Asp Ile Ile Val Leu Arg Asn Leu Asp Ile Leu Phe His
                165                 170                 175

Phe Pro Gln Met Ser Ala Thr Gly Asn Asp Val Trp Ile Phe Asn Ser
            180                 185                 190

Gly Ile Met Val Ile Glu Pro Ser Asn Cys Thr Phe Lys Ile Leu Met
            195                 200                 205

Asp Arg Arg Lys Glu Ile Ile Ser Tyr Asn Gly Gly Asp Gln Gly Phe
210                 215                 220

Leu Asn Glu Val Phe Val Trp Trp His Arg Leu Pro Arg Arg Val Asn
225                 230                 235                 240

Phe Leu Lys Asn Phe Trp Ala Asn Thr Thr Asn Glu Ala Ser Val Lys
                245                 250                 255

Asn Glu Leu Phe Gly Ala Asp Pro Lys Val Tyr Ser Ile His Tyr
            260                 265                 270

Leu Gly Leu Lys Pro Trp Leu Cys Tyr Arg Asp Tyr Asp Cys Asn Trp
            275                 280                 285

Asn Ile Gly Asp Gln Arg Val Tyr Ala Ser Asp Val Ala His Gln Arg
290                 295                 300

Trp Trp Lys Phe His Asp Ala Met Asp Glu Lys Leu Gln Lys Phe Cys
305                 310                 315                 320

Gly Leu Thr Lys Gln Arg Lys Ile Glu Leu Asp Trp Asp Arg Lys Met
                325                 330                 335

Ala Arg Lys Ser Gln Phe Ser Asp Glu His Trp Lys Ile Asn Val Thr
            340                 345                 350

Asp Pro Arg Arg Val His Leu Ile
            355                 360
```

<210> SEQ ID NO 18
<211> LENGTH: 649
<212> TYPE: PRT
<213> ORGANISM: Populus tremula x Populus tremuloides

<400> SEQUENCE: 18

-continued

```
Met Arg Gly Val Gly Val Thr Ser Pro Ser Ser Ser Ala Glu Pro
1               5                   10                  15

Arg His Arg Ser Ser Ala Phe Asn Glu Asp Ala Ser Arg Arg Phe
                20                  25                  30

Leu Arg Gly Arg Asp Leu Arg Asp Val Glu Lys Ala Phe Gln Val Pro
        35                  40                  45

Ile Gln Tyr Lys Asn Leu Asn Cys Lys Ile Ser Thr Leu Lys Val Val
    50                  55                  60

Leu Leu Ile Ile Ala Phe Gly Thr Leu Val Thr Phe Tyr His Ser Pro
65                  70                  75                  80

Val Val Tyr Ile Ala Asp Gln Pro Ser Thr Ser Gly Ser Arg Pro Ser
                85                  90                  95

Phe Val Asp Arg Trp Thr Arg Asp Gly Ala Ala Val Asp Pro Arg Tyr
                100                 105                 110

Ile Ser Asn Leu Asp Ile Asn Trp Asp Gln Ile Ser Asp Asn Ile Val
            115                 120                 125

Lys Leu Asp Asp Ser Asn Glu Tyr Gln Gly Ile Gly Leu Leu Asn Phe
        130                 135                 140

Asn Glu Ser Glu Ile Asn Asn Trp Lys Leu Met Leu Leu Asp Val Glu
145                 150                 155                 160

His Val Val Leu His Leu Glu His Val Ala Glu Asp Val Thr Trp Glu
                165                 170                 175

Ser Leu Tyr Pro Glu Trp Ile Asp Glu Glu Glu Phe Glu Val Pro
                180                 185                 190

Thr Cys Pro Val Leu Pro Lys Leu Lys Val Pro Gly Lys Pro Arg Ile
        195                 200                 205

Asp Ile Ile Ala Val Lys Leu Pro Cys Asn Lys Ser Gly Lys Trp Ser
    210                 215                 220

Arg Asp Val Ala Arg Leu His Leu Gln Leu Ala Ala Ala Asn Leu Ala
225                 230                 235                 240

Ala Ser Ala Lys Ser Tyr His Pro Val Arg Val Leu Leu Val Thr Asp
                245                 250                 255

Cys Phe Pro Thr Pro Asn Leu Phe Thr Cys Lys Glu Leu Ile Trp His
                260                 265                 270

Glu Gly Asn Leu Trp Met Tyr Gln Pro Asn Leu Asn Val Leu Arg Glu
            275                 280                 285

Lys Ile Gln Leu Pro Val Gly Ser Cys Glu Leu Ser Val Pro Leu Lys
        290                 295                 300

Ala Lys Glu His Phe Tyr Ser Glu Arg Ala His Arg Glu Ala Tyr Ala
305                 310                 315                 320

Thr Ile Leu His Ser Ala His Val Gly Val Cys Gly Ala Ile Ala Ala
                325                 330                 335

Ala Gln Ser Ile Arg Leu Ser Gly Ser Thr Arg Asp Leu Val Ile Leu
            340                 345                 350

Val Asp Glu Thr Ile Ser Val Tyr His Arg Ser Gly Leu Glu Ala Ala
        355                 360                 365

Gly Trp Lys Ile Arg Thr Ile Gln Arg Ile Arg Asn Pro Lys Ala Glu
    370                 375                 380

Lys Asp Ala Tyr Asn Glu Trp Asn Tyr Ser Lys Phe Arg Leu Trp Gln
385                 390                 395                 400

Leu Thr Asp Tyr Asp Lys Ile Ile Phe Ile Asp Ala Asp Leu Leu Ile
                405                 410                 415
```

```
Leu Arg Asn Ile Asp Phe Leu Phe Gly Met Pro Glu Ile Ser Ala Thr
            420                 425                 430

Gly Asn Asn Ala Thr Leu Phe Asn Ser Gly Val Met Val Ile Glu Pro
            435                 440                 445

Ser Asn Cys Thr Phe Asn Leu Leu Met Glu His Ile Asn Glu Ile Glu
450                 455                 460

Ser Tyr Asn Gly Gly Asp Gln Gly Tyr Leu Asn Glu Ile Phe Thr Trp
465                 470                 475                 480

Trp His Arg Ile Pro Lys His Met Asn Phe Leu Lys His Phe Trp Ile
                485                 490                 495

Gly Asp Glu Glu Val Lys Gln Lys Lys Thr Ser Leu Phe Gly Ala
            500                 505                 510

Glu Pro Pro Ile Leu Tyr Val Leu His Tyr Leu Gly Val Lys Pro Trp
            515                 520                 525

Leu Cys Phe Arg Asp Tyr Asp Cys Asn Trp Asn Val Asp Ile Phe Gln
            530                 535                 540

Glu Phe Ala Ser Asp Thr Ala His Glu Lys Trp Trp Arg Val Tyr Asp
545                 550                 555                 560

Ala Met Pro Glu Gln Leu His Gln Phe Cys Ser Leu Lys Ser Lys Gln
                565                 570                 575

Lys Ala Gln Leu Glu Tyr Asp Arg Arg Glu Ala Glu Lys Ala Asn Tyr
            580                 585                 590

Thr Asp Asp His Trp Lys Ile Lys Val Gln Asp Arg Leu Lys Lys
            595                 600                 605

Cys Ile Asp Asn Val Cys Asn Trp Lys Ser Met Leu Lys His Trp Gly
610                 615                 620

Glu Thr Asn Trp Thr Asp Asp Glu Phe Leu Asn Pro Ser Pro Pro Ala
625                 630                 635                 640

Ile Ser Thr Ala Ser Leu Ser Gly Leu
                645

<210> SEQ ID NO 19
<211> LENGTH: 636
<212> TYPE: PRT
<213> ORGANISM: Populus tremula x Populus tremuloides

<400> SEQUENCE: 19

Met Gly Gly Pro Pro Gly Ser Val Glu Ala Arg His Arg Leu Ser Ala
1               5                   10                  15

Ser Phe Glu Asp Leu Tyr Lys Arg Arg Leu Thr Arg Ser Lys Val Lys
                20                  25                  30

Gly Val Glu Lys Pro Phe Asn Ile Pro Ile Gln Asp Arg Ser Ser Cys
            35                  40                  45

Cys Lys Phe Pro Leu Ile Lys Phe Ile Leu Val Val Ile Ala Gly
    50                  55                  60

Thr Ile Val Ser Leu Leu Tyr Ser Pro Asp Val Asp Gln Leu Ser His
65                  70                  75                  80

Ser Gly Ser Arg Gln Asn Phe Val Asn Arg Trp Ile Trp Gly Gly Ser
                85                  90                  95

Asp Pro Arg Tyr Val Ser Asp Leu Asp Val Lys Trp Asp Asp Val Met
            100                 105                 110

Lys Val Ile Glu Lys Leu Gly Glu Gln Asn Asp Tyr Gln Gly Ile Gly
        115                 120                 125

Leu Leu Asn Phe Asn Asp Ser Glu Val Tyr Asn Trp Asn Gln Leu Thr
    130                 135                 140
```

```
Pro Asp Ala Thr His Val Asn Ile Gln Leu Asp Tyr Ala Asp Lys Asn
145                 150                 155                 160

Met Thr Trp Asp Ser Leu Tyr Pro Glu Trp Ile Asp Glu Glu Gln Glu
            165                 170                 175

Lys Glu Val Pro Val Cys Pro Ser Leu Pro Lys Pro Asp Thr Pro Arg
        180                 185                 190

Lys Arg Leu Asp Leu Ile Ala Val Lys Leu Pro Cys Arg Asn Glu Trp
        195                 200                 205

Asn Trp Ser Arg Asp Val Ala Arg Leu His Leu Gln Leu Ala Ala Ala
        210                 215                 220

Ser Leu Ala Ala Ser Ala Lys Gly Phe Tyr Pro Val His Met Leu Phe
225                 230                 235                 240

Ile Thr Arg Arg Phe Pro Ile Pro Asn Leu Phe Ser Cys Lys Glu Leu
                245                 250                 255

Val Val Arg Glu Gly Asn Val Trp Leu Tyr Lys Pro Asp Val Asn Val
            260                 265                 270

Leu Arg Gln Lys Leu His Leu Pro Val Gly Ser Cys Glu Leu Ala Leu
        275                 280                 285

Pro Leu Arg Asp Arg Ala Arg Ala Tyr Ser Gly Asn Pro Gln Arg Glu
290                 295                 300

Ala Tyr Ala Thr Ile Leu His Ser Ala His Val Tyr Val Cys Gly Ala
305                 310                 315                 320

Ile Ala Ala Ala Gln Ser Ile Arg Leu Ser Gly Ser Asn Arg Asp Leu
                325                 330                 335

Val Ile Leu Val Asp Glu Thr Ile Ser Val Tyr His Arg Ser Gly Leu
            340                 345                 350

Glu Ala Ala Gly Trp Lys Ile Arg Thr Ile Gln Arg Ile Arg Asn Pro
            355                 360                 365

Lys Ala Glu Lys Asp Ala Tyr Asn Glu Trp Asn Tyr Ser Lys Phe Arg
370                 375                 380

Leu Trp Gln Leu Thr Asp Tyr Asp Lys Ile Ile Phe Ile Asp Ala Asp
385                 390                 395                 400

Leu Leu Ile Leu Arg Asn Ile Asp Phe Leu Phe Gly Met Pro Glu Ile
                405                 410                 415

Ser Ala Thr Gly Asn Asn Ala Ser Leu Phe Asn Ser Gly Val Met Val
            420                 425                 430

Ile Glu Pro Ser Asn Cys Thr Phe Asn Leu Leu Met Glu His Ile Asn
            435                 440                 445

Glu Ile Glu Ser Tyr Asn Gly Gly Asp Gln Gly Tyr Leu Asn Glu Val
            450                 455                 460

Phe Thr Trp Trp His Arg Ile Pro Lys His Met Asn Phe Leu Lys His
465                 470                 475                 480

Phe Trp Ile Gly Asp Glu Glu Val Lys Gln Lys Lys Thr Arg Leu
                485                 490                 495

Phe Ala Ala Glu Pro Pro Ile Leu Tyr Val Leu His Tyr Leu Gly Val
            500                 505                 510

Lys Pro Trp Leu Cys Phe Arg Asp Tyr Asp Cys Asn Trp Asn Ala Asp
            515                 520                 525

Ile Phe Gln Glu Phe Ala Ser Asp Val Ala His Glu Lys Trp Trp Arg
        530                 535                 540

Val His Asp Ala Met Pro Glu Gln Leu His Gln Phe Cys Ser Leu Lys
545                 550                 555                 560
```

```
Ser Lys Gln Lys Ala Gln Leu Glu Phe Asp Arg Arg Glu Ala Glu Lys
            565                 570                 575

Ala Asn Tyr Thr Asp Gly His Trp Lys Ile Lys Val Gln Asp Arg Arg
        580                 585                 590

Leu Lys Lys Cys Val Asp Asn Val Cys Asn Trp Lys Ser Met Leu Lys
        595                 600                 605

His Trp Gly Glu Thr Asn Trp Thr Asn Asp Glu Phe Phe Asn Pro Ser
        610                 615                 620

Pro Pro Ala Ile Ser Thr Ala Ser Leu Pro Gly Leu
625                 630                 635

<210> SEQ ID NO 20
<211> LENGTH: 168
<212> TYPE: PRT
<213> ORGANISM: Picea abies

<400> SEQUENCE: 20

Trp Gln Leu Thr Asp Tyr Asp Lys Ile Ile Phe Ile Asp Ser Asp Leu
1               5                   10                  15

Leu Ile Leu Arg Asn Leu Asp Phe Leu Phe Asp Leu Pro Glu Ile Ser
            20                  25                  30

Ala Thr Gly Asn Ser Arg Phe Ile Phe Asn Ser Gly Met Met Val Ile
        35                  40                  45

Glu Pro Ser Asn Cys Thr Phe Arg Phe Leu Leu Gln His Arg Arg Asp
    50                  55                  60

Ile Val Ser Tyr Asn Gly Gly Asp Gln Gly Tyr Leu Asn Glu Val Phe
65                  70                  75                  80

Thr Trp Trp His Arg Ile Pro Lys Arg Met Asn Tyr Leu Lys His Phe
                85                  90                  95

Trp Ser Asn Asp Thr Glu Glu Phe Glu Met Lys Thr Ser Leu Phe Gly
            100                 105                 110

Ala Asp Pro Pro Glu Leu Tyr Val Leu His Tyr Leu Gly Ile Lys Pro
        115                 120                 125

Trp Leu Cys Tyr Arg Asp Tyr Asp Cys Asn Trp Asn Val Glu Asn Gln
    130                 135                 140

Arg Ala Tyr Ala Ser Asn Val Ala His Ala Arg Trp Trp Lys Ile His
145                 150                 155                 160

Asp Asn Met Pro Arg Gln Leu His
                165

<210> SEQ ID NO 21
<211> LENGTH: 623
<212> TYPE: PRT
<213> ORGANISM: Oryza sativa

<400> SEQUENCE: 21

Pro Gly Ala Val Cys His Trp His Gly Gly Asp Gly Arg Arg Arg Gly
1               5                   10                  15

Gly Arg Gln Ala Val Val Val Val Val Ala Gly Gly Gly Ala
            20                  25                  30

Glu Gly Gly Gly His Arg Glu Ala Glu Arg Gly Val Pro Arg Leu Leu
        35                  40                  45

Leu Pro Arg Val His Gly Ala Pro Pro Pro Gln Val Leu Leu Pro
    50                  55                  60

Pro Arg Pro Arg Arg Arg Leu Leu Pro Arg Pro Leu His Arg Leu Pro
65                  70                  75                  80
```

```
Arg Arg Leu His Pro Gly Asp Asp His Arg Pro Ala Leu Ser Glu
                85                  90                  95

Gly Lys Leu Gly Gly Val Ala Ala Asn Lys Ala Val Ala Ala Ala
            100                 105                 110

Glu Arg Ile Val Asn Ala Gly Arg Ala Pro Ala Met Phe Asp Glu Leu
            115                 120                 125

Arg Gly Arg Leu Arg Met Gly Leu Val Asn Ile Gly Arg Asp Glu Leu
            130                 135                 140

Leu Ala Leu Gly Val Glu Gly Asp Ala Val Gly Val Asp Phe Glu Arg
145                 150                 155                 160

Val Ser Asp Met Phe Arg Trp Ser Asp Leu Phe Pro Glu Trp Ile Asp
                165                 170                 175

Glu Glu Glu Asp Asp Glu Gly Pro Ser Cys Pro Glu Leu Pro Met Pro
            180                 185                 190

Asp Phe Ser Arg Tyr Gly Asp Val Asp Val Val Ala Ser Leu Pro
            195                 200                 205

Cys Asn Arg Ser Asp Ala Ala Trp Asn Arg Asp Val Phe Arg Leu Gln
    210                 215                 220

Val His Leu Val Thr Ala His Met Ala Ala Arg Lys Gly Leu Arg His
225                 230                 235                 240

Asp Ala Gly Gly Gly Gly Gly Gly Arg Val Arg Val Val Arg
                245                 250                 255

Ser Glu Cys Glu Pro Met Met Asp Leu Phe Arg Cys Asp Glu Ala Val
                260                 265                 270

Gly Arg Asp Gly Glu Trp Trp Met Tyr Met Val Asp Val Glu Arg Leu
            275                 280                 285

Glu Glu Lys Leu Arg Leu Pro Val Gly Ser Cys Asn Leu Ala Leu Pro
    290                 295                 300

Leu Trp Gly Pro Gly Gly Ile Gln Glu Val Phe Asn Val Ser Glu Leu
305                 310                 315                 320

Thr Ala Ala Ala Ala Thr Ala Gly Arg Pro Arg Arg Glu Ala Tyr Ala
                325                 330                 335

Thr Val Leu His Ser Ser Asp Thr Tyr Leu Cys Gly Ala Ile Val Leu
            340                 345                 350

Ala Gln Ser Ile Arg Arg Ala Gly Ser Thr Arg Asp Leu Val Leu Leu
        355                 360                 365

His Asp His Thr Val Ser Lys Pro Ala Leu Ala Ala Leu Val Ala Ala
    370                 375                 380

Gly Trp Thr Pro Arg Lys Ile Lys Arg Ile Arg Asn Pro Arg Ala Glu
385                 390                 395                 400

Arg Gly Thr Tyr Asn Glu Tyr Asn Tyr Ser Lys Phe Arg Leu Trp Gln
                405                 410                 415

Leu Thr Asp Tyr Asp Arg Val Val Phe Val Asp Ala Asp Ile Leu Val
            420                 425                 430

Leu Arg Asp Leu Asp Ala Leu Phe Gly Phe Pro Gln Leu Thr Ala Val
            435                 440                 445

Gly Asn Asp Gly Ser Leu Phe Asn Ser Gly Val Met Val Ile Glu Pro
450                 455                 460

Ser Gln Cys Thr Phe Gln Ser Leu Ile Arg Gln Arg Thr Ile Arg
465                 470                 475                 480

Ser Tyr Asn Gly Gly Asp Gln Gly Phe Leu Asn Glu Val Phe Val Trp
                485                 490                 495

Trp His Arg Leu Pro Arg Arg Val Asn Tyr Leu Lys Asn Phe Trp Ala
```

```
                    500                 505                 510
Asn Thr Thr Ala Glu Arg Ala Leu Lys Glu Arg Leu Phe Arg Ala Asp
                515                 520                 525

Pro Ala Glu Val Trp Ser Ile His Tyr Leu Gly Leu Lys Pro Trp Thr
            530                 535                 540

Cys Tyr Arg Asp Tyr Asp Cys Asn Trp Asn Ile Gly Asp Gln Arg Val
545                 550                 555                 560

Tyr Ala Ser Asp Ala Ala His Ala Arg Trp Trp Gln Val Tyr Asp Asp
                565                 570                 575

Met Gly Glu Ala Met Arg Ser Pro Cys Arg Leu Ser Glu Arg Arg Lys
            580                 585                 590

Ile Glu Ile Ala Trp Asp Arg His Leu Ala Glu Glu Ala Gly Phe Ser
                595                 600                 605

Asp His His Trp Lys Ile Asn Ile Thr Asp Pro Arg Lys Trp Glu
            610                 615                 620

<210> SEQ ID NO 22
<211> LENGTH: 635
<212> TYPE: PRT
<213> ORGANISM: Oryza sativa

<400> SEQUENCE: 22

Met Gly Ser Leu Glu Thr Thr Asn Thr Arg Tyr Arg Pro Ala Gly Ala
1               5                   10                  15

Ala Asp Asp Thr Ala Lys Arg Arg Thr Gln Lys Ser Lys Ser Phe Lys
                20                  25                  30

Glu Val Glu Lys Phe Asp Val Phe Leu Glu Lys Ser Ser Gly Cys
            35                  40                  45

Lys Phe Arg Ser Leu Gln Leu Leu Leu Phe Ala Ile Met Ser Ala Ala
50                  55                  60

Phe Leu Thr Leu Leu Tyr Thr Pro Ser Val Tyr Asp His Gln Met Gln
65                  70                  75                  80

Ser Ser Ser Arg Phe Val Ser Gly Trp Ile Trp Asp Lys Thr Ile Pro
                85                  90                  95

Asp Pro Arg Tyr Val Ser Ser Leu Gly Val Gln Trp Glu Asp Val Tyr
            100                 105                 110

Lys Thr Val Glu Asn Leu Asn Asp Gly Glu Arg Lys Leu Lys Val Gly
        115                 120                 125

Leu Leu Asn Phe Asn Ser Thr Glu Ile Gly Ser Trp Thr Gln Leu Leu
130                 135                 140

Pro Asp Ser Asp Phe Ser Ile Ile Arg Leu Glu His Ala Lys Glu Ser
145                 150                 155                 160

Ile Thr Trp Gln Thr Leu Tyr Pro Glu Trp Ile Asp Glu Glu Glu
                165                 170                 175

Thr Glu Ile Pro Ser Cys Pro Ser Leu Pro Asp Pro Ile Phe Pro Arg
            180                 185                 190

Gly Thr His Phe Asp Val Val Ala Val Lys Leu Pro Cys Thr Arg Ala
        195                 200                 205

Gly Gly Trp Ser Arg Asp Val Ala Arg Leu His Leu Gln Leu Ser Ala
    210                 215                 220

Ala Lys Val Ala Val Thr Ala Ser Arg Gly Asn Arg Gly Ile His Val
225                 230                 235                 240

Leu Phe Val Thr Asp Cys Phe Pro Ile Pro Asn Leu Phe Ser Cys Lys
                245                 250                 255
```

Asn Leu Val Lys His Glu Gly Asn Ala Trp Met Tyr Lys Pro Asp Leu
            260                 265                 270

Lys Ala Leu Arg Glu Lys Leu Arg Leu Pro Val Gly Ser Cys Glu Leu
            275                 280                 285

Ala Val Pro Leu Lys Ala Lys Ala Arg Leu Tyr Ser Val Asp Arg Arg
            290                 295                 300

Arg Glu Ala Tyr Ala Thr Ile Leu His Ser Ala Ser Glu Tyr Val Cys
305                 310                 315                 320

Gly Ala Ile Thr Ala Ala Gln Ser Ile Arg Gln Ala Gly Ser Thr Arg
                325                 330                 335

Asp Phe Val Ile Leu Val Asp Glu Thr Ile Ser Asn His His Arg Lys
            340                 345                 350

Gly Leu Glu Ala Ala Gly Trp Lys Val Arg Ile Ile Gln Arg Ile Arg
            355                 360                 365

Asn Pro Lys Ala Glu Arg Asp Ala Tyr Asn Glu Trp Asn Tyr Ser Lys
            370                 375                 380

Phe Arg Leu Trp Gln Leu Thr Asp Tyr Asp Lys Ile Ile Phe Ile Asp
385                 390                 395                 400

Ala Asp Leu Leu Ile Leu Arg Asn Val Asp Phe Leu Phe Ala Met Pro
                405                 410                 415

Glu Ile Thr Ala Thr Gly Asn Asn Ala Thr Leu Phe Asn Ser Gly Val
            420                 425                 430

Met Val Ile Glu Pro Ser Asn Cys Thr Phe Gln Leu Leu Met Asp His
            435                 440                 445

Ile Asn Glu Ile Thr Ser Tyr Asn Gly Gly Asp Gln Gly Tyr Leu Asn
450                 455                 460

Glu Ile Phe Thr Trp Trp His Arg Ile Pro Lys His Met Asn Phe Leu
465                 470                 475                 480

Lys His Phe Trp Glu Gly Asp Glu Glu Val Lys Val Lys Thr
                485                 490                 495

Arg Leu Phe Gly Ala Asp Pro Pro Ile Leu Tyr Val Leu His Tyr Leu
            500                 505                 510

Gly Leu Lys Pro Trp Leu Cys Phe Arg Asp Tyr Asp Cys Asn Trp Asn
            515                 520                 525

Asn Pro Ile Leu Arg Glu Phe Ala Ser Asp Val Ala His Ala Arg Trp
            530                 535                 540

Trp Lys Val His Asp Lys Met Pro Lys Lys Leu Gln His Tyr Cys Leu
545                 550                 555                 560

Leu Arg Ser Arg Gln Lys Ala Gly Leu Glu Trp Asp Arg Arg Gln Ala
                565                 570                 575

Glu Lys Ala Asn Phe Thr Asp Gly His Trp Arg Arg Asn Ile Thr Asp
            580                 585                 590

Pro Arg Leu Lys Thr Cys Phe Glu Lys Phe Cys Phe Trp Glu Ser Met
            595                 600                 605

Leu Trp His Trp Gly Glu Ser Lys Asn Ser Thr Lys Glu Asn Pro Val
            610                 615                 620

Pro Ala Thr Pro Thr Ala Ser Leu Thr Ser Ser
625                 630                 635

<210> SEQ ID NO 23
<211> LENGTH: 341
<212> TYPE: PRT
<213> ORGANISM: Oryza sativa

<400> SEQUENCE: 23

Met Gly Ser Leu Glu Thr Arg Tyr Arg Pro Ala Gly Pro Ser Asp
1               5                   10                  15

Asp Thr Thr Lys Arg Arg Thr Pro Lys Ser Arg Ile Tyr Lys Asp Val
                20                  25                  30

Glu Asn Phe Gly Val Leu Val Leu Glu Lys Asn Ser Gly Cys Lys Phe
            35                  40                  45

Lys Thr Leu Arg Tyr Leu Leu Leu Ala Ile Thr Ser Ala Thr Phe Leu
    50                  55                  60

Thr Leu Leu Thr Pro Thr Phe Tyr Glu His Gln Leu Gln Ser Ser Arg
65                  70                  75                  80

Tyr Val Asp Val Gly Trp Ile Trp Asp Lys Pro Ser Tyr Asp Pro Arg
                85                  90                  95

Tyr Val Ser Ser Val Asp Val Gln Trp Glu Asp Val Tyr Lys Ala Leu
                100                 105                 110

Glu Asn Leu Asn Asp Gly Ser Gln Lys Leu Lys Val Gly Leu Leu Asn
            115                 120                 125

Phe Asn Ser Thr Glu Tyr Gly Ser Trp Ala Gln Leu Leu Pro Gly Ser
    130                 135                 140

Ala Val Ser Ile Val Arg Leu Glu His Ala Lys Asp Ser Ile Thr Trp
145                 150                 155                 160

Asp Thr Leu Tyr Pro Glu Trp Ile Asp Glu Glu Glu Thr Asp Ile
                165                 170                 175

Pro Ala Cys Pro Ser Leu Pro Asp Pro Asn Val Arg Lys Gly Ser His
            180                 185                 190

Phe Asp Val Ile Ala Val Lys Leu Pro Cys Thr Arg Val Gly Gly Trp
    195                 200                 205

Ser Arg Asp Val Ala Arg Leu His Leu Gln Leu Ser Ala Ala Lys Leu
210                 215                 220

Ala Val Ala Ser Ser Lys Gly Asn Gln Lys Val His Val Leu Phe Val
225                 230                 235                 240

Thr Asp Cys Phe Pro Ile Pro Asn Leu Phe Pro Cys Lys Asn Leu Val
            245                 250                 255

Lys His Glu Gly Asn Ala Trp Leu Tyr Ser Pro Asp Leu Lys Ala Leu
    260                 265                 270

Arg Glu Lys Leu Arg Leu Pro Val Gly Ser Cys Glu Leu Ala Val Pro
    275                 280                 285

Leu Lys Ala Lys Asp Ser Thr Gln Trp Ile Glu Glu Lys His Met
290                 295                 300

Leu Leu Ser Cys Thr Gln Val Asn Met Ser Val Val Leu Ser Gln
305                 310                 315                 320

Gln Leu Lys Ala Phe Ala Lys Gln Gly Gln Leu Gly Ile Trp Leu Ser
            325                 330                 335

Leu Ser Met Thr Arg
            340

<210> SEQ ID NO 24
<211> LENGTH: 613
<212> TYPE: PRT
<213> ORGANISM: Oryza sativa

<400> SEQUENCE: 24

Met Gly Val Thr Gly Gly Ala Gly Glu Ala Val Lys Pro Ser Ser
1               5                   10                  15

Ser Ser Leu Ser Pro Val Ala Gly Leu Arg Ala Ala Ala Ile Val Lys

```
                    20                  25                  30
Leu Asn Ala Ala Phe Leu Ala Phe Phe Leu Ala Tyr Met Ala Leu
                35                  40                  45

Leu Leu His Pro Lys Tyr Ser Tyr Leu Leu Asp Arg Gly Ala Ala Ser
        50                  55                  60

Ser Leu Val Arg Cys Thr Ala Phe Arg Asp Cys Thr Pro Ala Thr
65                  70                  75                  80

Thr Thr Thr Ala Gln Leu Ser Arg Lys Leu Gly Gly Val Ala Ala Asn
                    85                  90                  95

Lys Ala Val Ala Ala Ala Glu Arg Ile Val Asn Ala Gly Arg Ala
            100                 105                 110

Pro Ala Met Phe Asp Glu Leu Arg Gly Arg Leu Arg Met Gly Leu Val
                115                 120                 125

Asn Ile Gly Arg Asp Glu Leu Leu Ala Leu Gly Val Glu Gly Asp Ala
            130                 135                 140

Val Gly Val Asp Phe Glu Arg Val Ser Asp Met Phe Arg Trp Ser Asp
145                 150                 155                 160

Leu Phe Pro Glu Trp Ile Asp Glu Glu Asp Glu Gly Pro Ser
                    165                 170                 175

Cys Pro Glu Leu Pro Met Pro Asp Phe Ser Arg Tyr Gly Asp Val Asp
                180                 185                 190

Val Val Val Ala Ser Leu Pro Cys Asn Arg Ser Asp Ala Ala Trp Asn
            195                 200                 205

Arg Asp Val Phe Arg Leu Gln Val His Leu Val Thr Ala His Met Ala
            210                 215                 220

Ala Arg Lys Gly Leu Arg His Asp Ala Gly Gly Gly Gly Gly Arg
225                 230                 235                 240

Val Arg Val Val Val Arg Ser Glu Cys Glu Pro Met Met Asp Leu Phe
                    245                 250                 255

Arg Cys Asp Glu Ala Val Arg Arg Asp Gly Glu Trp Trp Met Tyr Met
                260                 265                 270

Val Asp Val Glu Arg Leu Glu Glu Lys Leu Arg Leu Pro Val Gly Ser
            275                 280                 285

Cys Asn Leu Ala Leu Pro Leu Trp Gly Pro Gly Gly Ile Gln Glu Val
            290                 295                 300

Phe Asn Val Ser Glu Leu Thr Ala Ala Ala Thr Ala Gly Arg Pro
305                 310                 315                 320

Arg Arg Glu Ala Tyr Ala Thr Val Leu His Ser Ser Asp Thr Tyr Leu
                    325                 330                 335

Cys Gly Ala Ile Val Leu Ala Gln Ser Ile Arg Arg Ala Gly Ser Thr
                340                 345                 350

Arg Asp Leu Val Leu Leu His Asp His Thr Val Ser Lys Pro Ala Leu
            355                 360                 365

Ala Ala Leu Val Ala Ala Gly Trp Thr Pro Arg Lys Ile Lys Arg Ile
            370                 375                 380

Arg Asn Pro Arg Ala Glu Arg Gly Thr Tyr Asn Glu Tyr Asn Tyr Ser
385                 390                 395                 400

Lys Phe Arg Leu Trp Gln Leu Thr Asp Tyr Asp Arg Val Phe Val
                    405                 410                 415

Asp Ala Asp Ile Leu Val Leu Arg Asp Leu Asp Ala Leu Phe Gly Phe
                420                 425                 430

Pro Gln Leu Thr Ala Val Gly Asn Asp Gly Ser Leu Phe Asn Ser Gly
            435                 440                 445
```

```
Val Met Val Ile Glu Pro Ser Gln Cys Thr Phe Gln Ser Leu Ile Arg
    450                 455                 460

Gln Arg Arg Thr Ile Arg Ser Tyr Asn Gly Gly Asp Gln Gly Phe Leu
465                 470                 475                 480

Asn Glu Val Phe Val Trp Trp His Arg Leu Pro Arg Arg Val Asn Tyr
                485                 490                 495

Leu Lys Asn Phe Trp Ala Asn Thr Thr Ala Glu Arg Ala Leu Lys Glu
                500                 505                 510

Arg Leu Phe Arg Ala Asp Pro Ala Glu Val Trp Ser Ile His Tyr Leu
            515                 520                 525

Gly Leu Lys Pro Trp Thr Cys Tyr Arg Asp Tyr Asp Cys Asn Trp Asn
        530                 535                 540

Ile Gly Asp Gln Arg Val Tyr Ala Ser Asp Ala Ala His Ala Arg Trp
545                 550                 555                 560

Trp Gln Val Tyr Asp Asp Met Gly Glu Ala Met Arg Ser Pro Cys Arg
                565                 570                 575

Leu Ser Glu Arg Arg Lys Ile Glu Ile Ala Trp Asp Arg His Leu Ala
            580                 585                 590

Glu Glu Ala Gly Phe Ser Asp His His Trp Lys Ile Asn Ile Thr Asp
        595                 600                 605

Pro Arg Lys Trp Glu
    610
```

<210> SEQ ID NO 25
<211> LENGTH: 614
<212> TYPE: PRT
<213> ORGANISM: Oryza sativa

<400> SEQUENCE: 25

```
Met Gly Val Thr Gly Gly Ala Gly Glu Ala Val Lys Pro Ser Ser Ser
1               5                   10                  15

Ser Ser Leu Ser Pro Val Ala Gly Leu Arg Ala Ala Ala Ile Val Lys
            20                  25                  30

Leu Asn Ala Ala Phe Leu Ala Phe Phe Phe Leu Ala Tyr Met Ala Leu
        35                  40                  45

Leu Leu His Pro Lys Tyr Ser Tyr Leu Leu Asp Arg Gly Ala Ala Ser
    50                  55                  60

Ser Leu Val Arg Cys Thr Ala Phe Arg Asp Ala Cys Thr Pro Ala Thr
65                  70                  75                  80

Thr Thr Thr Ala Gln Leu Ser Arg Lys Leu Gly Gly Val Ala Ala Asn
                85                  90                  95

Lys Ala Val Ala Ala Ala Glu Arg Ile Val Asn Ala Gly Arg Ala
            100                 105                 110

Pro Ala Met Phe Asp Glu Leu Arg Gly Arg Leu Arg Met Gly Leu Val
        115                 120                 125

Asn Ile Gly Arg Asp Glu Leu Leu Ala Leu Gly Val Glu Gly Asp Ala
    130                 135                 140

Val Gly Val Asp Phe Glu Arg Val Ser Asp Met Phe Arg Trp Ser Asp
145                 150                 155                 160

Leu Phe Pro Glu Trp Ile Asp Glu Glu Asp Glu Gly Pro Ser
                165                 170                 175

Cys Pro Glu Leu Pro Met Pro Asp Phe Ser Arg Tyr Gly Asp Val Asp
            180                 185                 190

Val Val Val Ala Ser Leu Pro Cys Asn Arg Ser Asp Ala Ala Trp Asn
```

```
            195                 200                 205
Arg Asp Val Phe Arg Leu Gln Val His Leu Val Thr Ala His Met Ala
210                 215                 220

Ala Arg Lys Gly Leu Arg His Asp Ala Gly Gly Gly Gly Gly Gly Gly
225                 230                 235                 240

Arg Val Arg Val Val Arg Ser Glu Cys Glu Pro Met Met Asp Leu
                245                 250                 255

Phe Arg Cys Asp Glu Ala Val Gly Arg Asp Gly Glu Trp Trp Met Tyr
            260                 265                 270

Met Val Asp Val Glu Arg Leu Glu Glu Lys Leu Arg Leu Pro Val Gly
        275                 280                 285

Ser Cys Asn Leu Ala Leu Pro Leu Trp Gly Pro Gly Gly Ile Gln Glu
    290                 295                 300

Val Phe Asn Val Ser Glu Leu Thr Ala Ala Ala Thr Ala Gly Arg
305                 310                 315                 320

Pro Arg Arg Glu Ala Tyr Ala Thr Val Leu His Ser Ser Asp Thr Tyr
                325                 330                 335

Leu Cys Gly Ala Ile Val Leu Ala Gln Ser Ile Arg Arg Ala Gly Ser
                340                 345                 350

Thr Arg Asp Leu Val Leu Leu His Asp His Thr Val Ser Lys Pro Ala
        355                 360                 365

Leu Ala Ala Leu Val Ala Ala Gly Trp Thr Pro Arg Lys Ile Lys Arg
370                 375                 380

Ile Arg Asn Pro Arg Ala Glu Arg Gly Thr Tyr Asn Glu Tyr Asn Tyr
385                 390                 395                 400

Ser Lys Phe Arg Leu Trp Gln Leu Thr Asp Tyr Asp Arg Val Val Phe
                405                 410                 415

Val Asp Ala Asp Ile Leu Val Leu Arg Asp Leu Asp Ala Leu Phe Gly
                420                 425                 430

Phe Pro Gln Leu Thr Ala Val Gly Asn Asp Gly Ser Leu Phe Asn Ser
            435                 440                 445

Gly Val Met Val Ile Glu Pro Ser Gln Cys Thr Phe Gln Ser Leu Ile
        450                 455                 460

Arg Gln Arg Arg Thr Ile Arg Ser Tyr Asn Gly Gly Asp Gln Gly Phe
465                 470                 475                 480

Leu Asn Glu Val Phe Val Trp Trp His Arg Leu Pro Arg Arg Val Asn
                485                 490                 495

Tyr Leu Lys Asn Phe Trp Ala Asn Thr Thr Ala Glu Arg Ala Leu Lys
            500                 505                 510

Glu Arg Leu Phe Arg Ala Asp Pro Ala Glu Val Trp Ser Ile His Tyr
        515                 520                 525

Leu Gly Leu Lys Pro Trp Thr Cys Tyr Arg Asp Tyr Asp Cys Asn Trp
    530                 535                 540

Asn Ile Gly Asp Gln Arg Val Tyr Ala Ser Asp Ala Ala His Ala Arg
545                 550                 555                 560

Trp Trp Gln Val Tyr Asp Asp Met Gly Glu Ala Met Arg Ser Pro Cys
                565                 570                 575

Arg Leu Ser Glu Arg Arg Lys Ile Glu Ile Ala Trp Arg His Leu
                580                 585                 590

Ala Glu Glu Ala Gly Phe Ser Asp His His Trp Lys Ile Asn Ile Thr
        595                 600                 605

Asp Pro Arg Lys Trp Glu
    610
```

<210> SEQ ID NO 26
<211> LENGTH: 2679
<212> TYPE: DNA
<213> ORGANISM: Hordeum vulgare

<400> SEQUENCE: 26

| | | | | | | |
|---|---|---|---|---|---|---|
| gctggtagag | agagggagcc | ggagccacac | accagcgcac | agccaccacc | accaccgact | 60 |
| gcgtccgtcc | atccgtctct | tcttcctcat | cctgccatcg | ccattgccgc | cgccgcagct | 120 |
| tcctcctccg | cagctgcgat | acggatgaga | agcagcgcga | ccggggcagc | gactgcgcgg | 180 |
| tcggcctgag | gaccggagag | gcaggccggc | gggctgcaga | gctcagctca | gctcagagga | 240 |
| ggcttcaacc | aggcagactg | aaaccgagcc | cccatgggct | ccctggaggc | gcggtaccgg | 300 |
| ccggccggag | cagctgatga | cacagctaaa | gaaggaccc | agaaaagtaa | aagtttcaaa | 360 |
| gaggttgaaa | agtttgatgt | atttgttcta | gagaaaagct | ctggctgcaa | gttccgttcc | 420 |
| ttgcaacttt | tgctcttcgc | tatcatgtct | gctgcatttc | tgacacttct | atacacacca | 480 |
| tctgtgtatg | agcatcagtt | gcagtccaat | tctcggtttg | ttaatgtcgg | atggatatgg | 540 |
| gataagacta | tccctgatcc | gagatatgta | tcttctatgg | ccgtccagtg | ggatgatgtg | 600 |
| tataaaacta | tcgaaagtct | gaatggtggt | gagcagaagc | tcaaagtcgg | actcttaaat | 660 |
| tttaacagca | ctgagttcgg | gtcttggaca | caattgctcc | cagaaagtga | gttttcgatc | 720 |
| ataaggttag | agcatgctaa | tgaaagcatt | acctggcaga | cgctgtatcc | tgaatggatt | 780 |
| gatgaggagg | aagaaacaga | gataccatct | tgtccatcgc | tttcagagcc | taatttccca | 840 |
| agaggcacgc | attttgatgt | tattgctgtg | aagcttccct | gtacccgagt | tggggggtgg | 900 |
| tcaagagatg | ttgcgcggtt | gcatctgcag | ttgtcagcag | caaaattggc | cgtgagtgcc | 960 |
| gctagaggca | accgtggggt | acatgtgatg | tttgtgacgg | agtgcttccc | tcttccgaat | 1020 |
| ctcttctctt | gcaagaatct | taagaaacat | gaaggcaatg | cttggctata | caagcctgat | 1080 |
| ccgaaggctt | taaggagaa | gcttagactt | ccaattggat | cttgtgagct | tgctgttcca | 1140 |
| ctcaaagcaa | aatcaagact | tttctcggta | gaccgacgca | gagaagcata | tgctaccata | 1200 |
| ctgcattcag | caagtgagta | tgtctgtggt | gcaatcgcag | cagctcaaag | cattcgtcaa | 1260 |
| gcaggatcaa | caagggactt | tgttattctt | gtcgatgaca | ccataagtga | ccatcaccga | 1320 |
| aagggccttg | aatctgcggg | ttggaaggtc | agaataattg | agaggatccg | gaaccccgaag | 1380 |
| gccgagcgtg | atgcttacaa | tgagtggaac | tacagcaagt | tccggttgtg | gcagctcacg | 1440 |
| gactatgaca | agatcatatt | catagatgct | gatctgctca | tcttgaggaa | cattgatttc | 1500 |
| ctgtttacaa | tgccagaaat | cagtgcaacc | ggcaacaatg | caacactctt | caactctggt | 1560 |
| gtcatggtca | tcgaaccctc | aaactgcaca | ttccagctgt | taatgagca | catcaatgag | 1620 |
| ataacatctt | acaatggtgg | tgatcagggc | tacttgaatg | agatattcac | atggtggcat | 1680 |
| cggattccca | agcacatgaa | cttcctgaag | catttctggg | agggtgatga | agaggaggtg | 1740 |
| aaggcgaaga | gacccagct | gtttggcgcc | aacccaccga | tcctctacgt | cctccactac | 1800 |
| ctgggccgca | aaccatggct | atgcttccgg | gactatgact | gcaactggaa | cgttccgata | 1860 |
| ctgcgggagt | ttgccagcga | cattgcgcac | acccggtggt | ggaaggtgca | tgacaagatg | 1920 |
| cccaagaagc | tccagagcta | ctgcctgctg | aggtcaaggc | tgaaggccgg | gctggagtgg | 1980 |
| gagcggaggc | aggcagagaa | ggccaacttc | accgacgggc | actggaagcg | gaacatcacg | 2040 |
| gacaagaggc | tcaagatttg | cttcgagaag | ttctgcttct | gggagagcat | gctgtggcac | 2100 |

| | |
|---|---|
| tggggtgagg cccccaactc gacgaagaag gcctcgacgc cggcactgcc caccgcgacc | 2160 |
| ctctcaagct catgatggga tgttgtgtag atattatcct ccccgagaaa ttttagcata | 2220 |
| ccagaagata cagcagactc ccagtctctc cttgatacat acacaatagc aacagcttgt | 2280 |
| aaaggtagcc atgctgctcc tagggctttc ctcaacagct atacattttg tttgctgcca | 2340 |
| atgccttggg gtcgcgctct cgttgctgct gctgctgccg ctccaaccgc gacggctaac | 2400 |
| gatttttttgg ttgatggatg gatggataat aattcgtcgc gtgtaggtaa attttcttgg | 2460 |
| gcaagacttg tctatggctc tgcgttggtg cagcagtagt tagcttttgt aatgtaatgt | 2520 |
| aatgtatggt ggttgtcgaa ctgttggttc cggcggcgtt ggtctggggt gatgcaaggt | 2580 |
| tcatattttg ctgaccggcg gacgccgccg tttctccttt ttggcaccat ggatgatgga | 2640 |
| catgaacatg atgatgttgt aatggaaaaa aaaaaaaaa | 2679 |

<210> SEQ ID NO 27
<211> LENGTH: 1879
<212> TYPE: DNA
<213> ORGANISM: Zea mays
<220> FEATURE:
<221> NAME/KEY: misc_feature
<222> LOCATION: (175)..(197)
<223> OTHER INFORMATION: n is a, c, g, or t
<220> FEATURE:
<221> NAME/KEY: misc_feature
<222> LOCATION: (1208)..(1249)
<223> OTHER INFORMATION: n is a, c, g, or t

<400> SEQUENCE: 27

| | |
|---|---|
| cctaagaagc ggtaaccgcc agagtcatct cagagttggg ctcttgaatt tcaacagcac | 60 |
| cgagtatggc tcctggacgc agttgctccc agctgacagc cacgttatct ccactgtaag | 120 |
| gctcgagcac gccaaggaca gcgtcacctg cagacgctg tacccctgagt ggatnnnnnn | 180 |
| nnnnnnnnnn nnnnnntac cctcttgccc gtcgctgccg gagccaaacg tgccaagagg | 240 |
| tgcgcgcttt gacgtcgtcg ccgtgaagct cccatgcacc cgtgtggcgg gctggtcgag | 300 |
| agacgtcgcg cggctccatc tgcagctctc ggcagccaaa ctggctgtgg cgtcctcgaa | 360 |
| gcgcaaccac gacgtccatg ttctcttcgt cactgactgc ttcccgatcc cgaacctctt | 420 |
| cccttgcaag aaccttgtca cacgtgaagg cagcacgagg ttgtacagtc ctgactccaa | 480 |
| ggcgttgagg gaaaagctca ggcttccagt cgggtcctgt gagcttgccg ttccactcaa | 540 |
| agccaaatcg aggcttttct cggtagatcg acgaagagaa gcgtacgcga cgatactgca | 600 |
| ttcagcgagc gaatacgtct gcggcgcaat tcggcagcg caaagcatcc gccaggcagg | 660 |
| atccaccagg gacctggtca tccttgtgga cgagaccata agcgaccacc accggagagg | 720 |
| cttggaggcg gcggggtgga aggtcagagt gatccagagg atcaggaacc caaggcgga | 780 |
| gcgcgacgcg tacaacgagt ggaactacag caagttcagg ctgtggcagc tcaccgacta | 840 |
| cgacaaggtc atcttcatag acgccgacct cctcatcctg aggaacgtcg acttcctgtt | 900 |
| cgccatgccg gagatcgccg cgacgggcaa caacgccacg ctcttcaact ccggcgtcat | 960 |
| ggtcgtcgag ccctccaact gcacgttccg cctgctcatg gaccacatcg acgagatcac | 1020 |
| ctcgtacaac ggcggggacc aggggtacct caacgagata ttcacgtggt ggcaccgcgt | 1080 |
| ccccaggcac atgaacttcc tcaagcactt ctgggagggc gacagcgagg ccatgaaggc | 1140 |
| gaagaagacc cagctgttcg gtgcggaccc gccggtcctc tacgtcctcc actaccttgg | 1200 |
| cctcaagnnn nnnnnnnnn nnnnnnnnnn nnnnnnnnnn nnnnnnnnng ccgggatgcg | 1260 |
| cgagttcgcc agcgacgtcg cgcatgcccg gtggtggaag gtgcacgaca ggatgccccg | 1320 |

-continued

```
gaagctccag tcctactgcc tgctgaggtc gcggcagaag gccaggctgg agtgggaccg      1380
gaggcaggcc gagaaggcca actctcaaga tggccactgg cgcctcaacg tcacggacac      1440
caggctcaag acgtgctttg agaagttctg cttctgggag agcatgctct ggcattgggg      1500
cgagaacagt aacaggacca agagcgtccc catggcagcc acgacggcaa ggtcgtgatc      1560
tgtagatata cgaacacccc atccccatat ggcaaccata catgcatagc aatagcttgt      1620
ataggtagct atgctttagt tcttcgctat atatacagaa tacaccactc gatccctgtt      1680
gttgtcaagg ctgcagctct atgtcgctgc cggcctgcca ccatggctaa cgattctttt      1740
gggttggctg ctgtaataag tttcaggtac atgtaaattt ccctgctgaa attacgtgac      1800
cgcgtgtgag aaatgaattt gtacagggcg ccaaataata attggttggt gcatacaaca      1860
tatgaccagt cttttgcag                                                   1879
```

<210> SEQ ID NO 28
<211> LENGTH: 596
<212> TYPE: PRT
<213> ORGANISM: Medicago truncatula

<400> SEQUENCE: 28

```
Met Asp Val Ser Asn Leu His Lys Leu Val Lys Thr Ala Pro Ser Lys
1               5                   10                  15

Ala Leu Ile Met Arg Phe Asn Leu Leu Cys Leu Ser Ile Phe Leu Ile
            20                  25                  30

Val Tyr Ala Thr Leu Leu Arg Pro Ser Ser Val Tyr Phe Asp
        35                  40                  45

Asn Ala Ala Ser Leu Val Arg Cys Ser Leu Arg Glu Cys His His Lys
    50                  55                  60

Gly Glu Asp Ser Met Lys Met Lys Ala Val Leu Glu Glu Leu Pro Lys
65                  70                  75                  80

Ala Lys Ser Arg Asn Pro Lys Asn Gly Thr Lys Ile Glu Val Pro Ser
                85                  90                  95

Phe Leu Gly Glu Lys Ile Gly Lys Gly Ile Lys Ile Gly Met Val Asn
            100                 105                 110

Met Asp Glu Asp Asp Val Ser Glu Trp Asn Val His Gly Glu Thr
        115                 120                 125

Ile Pro Ile Asn Phe Asp Lys Val Ser Gln Phe Phe Asn Trp Thr Asp
    130                 135                 140

Leu Phe Pro Glu Trp Ile Asp Glu Glu Glu Ser Asp Val Pro Thr
145                 150                 155                 160

Cys Pro Glu Leu Pro Met Pro Glu Phe Ala Thr Tyr Glu Asn Met Asp
                165                 170                 175

Ile Ile Val Ala Lys Leu Pro Cys Lys Tyr Pro Leu Glu Gly Trp Gly
            180                 185                 190

Arg Glu Val Leu Arg Leu Gln Val His Leu Ile Val Ala Asn Met Val
        195                 200                 205

Val Lys Lys Gly Lys Lys Asp Trp Lys Trp Lys Ser Lys Val Val Phe
    210                 215                 220

Trp Ser Lys Cys Arg Pro Met Leu Glu Ile Phe Arg Cys Asp Asp Leu
225                 230                 235                 240

Val Lys His Glu Gly Asp Trp Trp Phe Tyr Glu Val Asp Val Lys Lys
                245                 250                 255

Leu Glu Gln Lys Ile Ser Leu Pro Val Gly Ser Cys Asn Leu Ala Leu
            260                 265                 270
```

-continued

```
Pro Leu Trp Glu Gln Gly Ile Asp Lys Val Tyr Asp Ile Ser Lys Met
        275                 280                 285

Glu Gln Asn Val Arg Ser Lys Thr Arg Ala Lys His Glu Ala Tyr Ala
    290                 295                 300

Thr Val Leu His Ser Ser Glu Ser Tyr Val Cys Gly Ala Ile Thr Leu
305                 310                 315                 320

Ala Gln Ser Leu Leu Lys Thr Gly Thr Asn Arg Asp Leu Ile Leu Leu
                325                 330                 335

Ile Asp Ser Ser Ile Ser Val Arg Lys Arg Ala Leu Ala Gly Ala
                340                 345                 350

Gly Trp Lys Ile Arg Thr Ile Thr Arg Ile Arg Asn Pro Arg Ala Glu
        355                 360                 365

Asn Gly Thr Tyr Asn Glu Tyr Asn Tyr Ser Lys Phe Arg Leu Trp Gln
    370                 375                 380

Leu Thr Asp Tyr Glu Lys Ile Ile Phe Ile Asp Ser Asp Ile Leu Val
385                 390                 395                 400

Leu Arg Asn Leu Asp Ile Leu Phe Asn Phe Pro Gln Met Ser Ala Thr
                405                 410                 415

Gly Asn Asp Gln Ser Ile Phe Asn Ser Gly Ile Met Val Ile Glu Pro
                420                 425                 430

Ser Asn Cys Thr Phe Ser Val Leu Met Ser Arg Arg His Asp Ile Val
            435                 440                 445

Ser Tyr Asn Gly Gly Asp Gln Gly Phe Leu Asn Glu Ile Phe Val Trp
    450                 455                 460

Trp His Arg Leu Pro Arg Val Asn Tyr Leu Lys Asn Phe Trp Ala
465                 470                 475                 480

Asn Thr Thr Val Glu Ala Ser Val Lys Asn Gly Leu Phe Ala Ala Asp
                485                 490                 495

Pro Pro Lys Leu Tyr Ala Ile His Tyr Leu Gly Leu Lys Pro Trp His
            500                 505                 510

Cys Tyr Arg Asp Tyr Asp Cys Asn Trp Asp Val Met Asp Gln Arg Val
        515                 520                 525

Tyr Ala Ser Asp Val Ala His Gln Arg Trp Trp Asn Phe His Asp Arg
    530                 535                 540

Met Asp Lys Lys Leu Gln Ser Phe Cys Arg Leu Thr Arg Gln Arg Arg
545                 550                 555                 560

Thr Glu Leu Asn Trp Glu Arg Arg Ser Asn Lys Met Gly Ser Leu
                565                 570                 575

Asp Tyr His Trp Arg Ile Asn Val Thr Asp Pro Arg Lys Ser Gly Ser
            580                 585                 590

Leu Leu Met Asp
        595
```